United States Patent
Erb et al.

(10) Patent No.: US 6,251,688 B1
(45) Date of Patent: Jun. 26, 2001

(54) METHOD AND APPARATUS FOR MEASUREMENT OF BINDING BETWEEN A PROTEIN AND A NUCLEOTIDE

(75) Inventors: Judith L. Erb; James G. Downward; John R. Erb-Downward; Otho Ulrich, all of Ann Arbor, MI (US)

(73) Assignee: IA, Inc., Ann Arbor, MI (US)

( * ) Notice: Subject to any disclaimer, the term of this patent is extended or adjusted under 35 U.S.C. 154(b) by 0 days.

(21) Appl. No.: 09/045,223

(22) Filed: Mar. 20, 1998

(51) Int. Cl.[7] .................................................. G01N 33/543
(52) U.S. Cl. ........................... 436/518; 385/12; 385/15; 385/25; 385/123; 385/129; 385/130; 422/55; 422/57; 422/82.05; 422/82.08; 422/82.11; 435/6; 435/7.9; 435/287.1; 435/287.2; 435/287.9; 435/288.7; 435/808; 436/164; 436/172; 436/510; 436/524; 436/527; 436/65; 436/805; 436/814; 436/817; 436/818
(58) Field of Search .................................. 385/12, 15, 25, 385/123, 129, 130; 422/55, 57, 82.05, 82.08, 82.11; 435/6, 7, 9, 287.1, 287.2, 287.9, 288.7, 808; 436/510, 518, 524, 527, 65, 164, 172, 805, 814, 817, 818

(56) References Cited

U.S. PATENT DOCUMENTS

| | | | |
|---|---|---|---|
| 4,558,014 | * 12/1985 | Hirschfeld et al. | 436/527 |
| 4,608,344 | * 8/1986 | Carter et al. | 436/34 |
| 4,978,503 | * 12/1990 | Shanks et al. | 422/58 |
| 5,082,630 | * 1/1992 | Partin et al. | 422/82.05 |

* cited by examiner

Primary Examiner—Christopher L. Chin
(74) Attorney, Agent, or Firm—Kohn & Associates

(57) ABSTRACT

A method and apparatus for measuring binding between a plurality of molecules of a first type and a plurality of molecules of a second type is presented. Apparatus utilizes a sensor possessing a waveguide to which have been attached in close proximity to its surface, features resembling molecules of said first type. Light is injected into said waveguide so as to produce an evanescent field at its surface. Molecules of said second type are tagged with a tag belonging to that class of chemicals which alters a characteristic of light, when said light passes through said chemical tag. Apparatus utilizes a rapid means of monitoring the change in optical signal coming from said waveguide as binding proceeds between tagged molecules of type 2 and the feature resembling molecules of type 1 on said waveguide. This allows direct measurement of binding and dissociation rates between the two types of molecules. Methods are provided whereby such data may be used to compute affinity constants, binding activity, complex affinity constants resulting from cooperativity, and kinetic parameters for the molecular pair. Preferred embodiments of the invention illustrate application of the method and apparatus to measuring binding between biological receptors and their nuclear response elements, and the use of this type of measurement for assessment of the activity of hormonal mimics present in a sample, for evaluation of pharmaceuticals intended to treat hormone dependent cancers, and for evaluation of tissue biopsy samples to detect mutant forms of the p53 protein.

45 Claims, 4 Drawing Sheets

METHOD AND APPARATUS FOR MEASUREMENT OF BINDING BETWEEN A PROTEIN AND A NUCLEOTIDE

GOVERNMENT SUPPORT

This invention was made government support under NIH Grant ES06629 and NIH Grant ES07471 awarded by the National Institute of Health and Army Contract Number DAMD17-97-C-7033 awarded by the Army. The government has certain rights in the invention.

BACKGROUND OF THE INVENTION

1. Field of the Invention

This invention relates to an apparatus and a method for measuring binding between two molecular components resembling biologically active molecules or fragments thereof, such as and without limitation, binding between a specific protein and a specific nucleotide or G-protein. In one embodiment, the affinity of said binding is modulated by the binding of one molecular component to a third molecule. It is the sense of the present invention that said third molecule does not compete with binding between the first two components, but rather said third molecule induces a change in one of the first two components which results in a change in affinity between said molecular components. In another embodiment, measurement of binding between a protein component and its intended DNA response element is in itself of value. The apparatus and method of the present invention are of a type known by those skilled in the art as evanescent sensor fluorometry, and represents an improvement upon the apparatus and method described in U.S. patent application Ser. No. 08/616,576 entitled Surface Treatment and Light Injection Method and Apparatus which is assigned to the assignee of the present invention. As such, the apparatus described in the present invention can be equally well applied to immunoassay, which was the application toward which the apparatus of the previous patent application was directed.

The method of the present invention has particular relevance to study of the effect of certain test compounds, such as and without limitation, hormone mimics, on biological signal transduction which is mediated by binding of biological receptors and/or regulatory molecules to subsequent molecules such as and without limitation DNA molecules, involved in the transduction mechanism. The word "receptor" is defined for purpose of this invention according to the definition appearing in *Illustrated Dictionary of Immunology*, edited by Julius M. Cruse and Robert E. Lewis and published by CRC Press, Boca Raton, 1995, p.258, ISBN 0-8493-4557-X: "A molecular configuration on a cell or macromolecule that combines with molecules that are complementary to it." The term "regulatory molecule" is defined "a molecule which, upon binding to a specific complementary molecule, initiates a sequence of events resulting in regulation of a biological process."

In a first embodiment, the apparatus and method utilizing the principles of the invention are adapted for use as a screening tool for recognizing the presence of estrogen mimics in a sample. In a second embodiment the apparatus and method utilizing the principles of the invention are adapted for measuring estrogen receptor content in a tissue biopsy sample and evaluating in vitro the probable response of cancer cells, of a type present in that tissue biopsy sample, to certain pharmacologic agents which act through receptor binding. In a third embodiment, the apparatus and method utilizing the principles of the invention are adapted for evaluating the competency of the p53 protein present in a tissue sample.

2. Background to the Invention

Many biological processes are regulated by the binding of regulatory molecules such as hormones, neurotransmitters or cytokines to specific biological receptor molecules. Upon binding to the regulatory molecule, the receptor activates the next step in a signal transduction mechanism by itself binding to another molecular component of the transduction mechanism such as a nuclear response element or G-protein. The affinity with which this second stage of receptor binding occurs, or in some cases, whether or not this second stage binding occurs at all, is affected by the binding of the regulatory molecule to the receptor. A review of such mechanisms can be found in an article entitled "Mechanisms of Signal Transduction: Sex Hormones, Their Receptors and Clinical Utility" by James L. Wittliff and Wolfgang Raffelsberger, which appeared in *Journal of Clinical Ligand Assay*, Volume 18, Number 4, Winter, 1995. This text is fully and completely incorporated herein by reference, word for word and paragraph for paragraph.

There are many benefits which derive from the study of both the binding of receptors to regulatory molecules and the second stage binding of the receptors to another component of the signal transduction mechanism. Such study can assist in the design of drugs which exert their biological effect through binding to biological receptors. It can also lead to recognition of compounds in the environment which have the capacity to disrupt important biological regulatory mechanisms by virtue of the ability of such molecules to bind to molecular receptors. It is believed that the presence of such molecules in the environment plays a role in the development of a variety of disease types including cancer, immune dysfunctions, and reproductive problems.

Current methods used for studying these binding phenomena are described in the previously cited review. Because the methods require physical separation of bound from unbound molecules, the methods are quite time consuming and do not have the capacity to provide real-time data while binding is occurring between a receptor and a regulatory molecule or between receptors and another component of the signal transduction mechanism. The reliance of current methods on radiolabeled ligands also limits the circumstances under which such measurements can be made. The apparatus and method of the present invention overcomes the limitations of the prior art by removing the need to separate bound from unbound molecules prior to performing a measurement, with the consequence that real time binding between components can be monitored and association and dissociation constants and equilibrium constants can be calculated far more quickly and easily.

The apparatus of the invention is a type of evanescent fiber optic sensor. Evanescent fiber optic sensors provide a method whereby a molecule bearing a fluorescent tag can be directly monitored as it binds to a binding partner attached to an optical fiber. Light traveling through an optical fiber at or near the critical angle is totally internally reflected so that it does not excite fluorescence in the surrounding solution. Total internal reflection does, however, produce an evanescent field which extends about 1000 angstroms from the surface of the fiber. This means that fluorescence of molecules binding to the surface of the fiber can be excited without exciting fluorescence of unbound molecules in the surrounding solution. Therefore measurement of binding can be made without the necessity for physical separation of bound from unbound molecules. Evanescent sensors based upon measurement at a certain time of fluorescent antigen bound to antibodies on the fiber have been used to perform immunoassays by calculating concentrations of antigen in a solution. These have been reported in literature and patents and are thoroughly described in the book *Biosensors with Fiber Optics,* Donald L. Wise and Lemuel B. Wingard, Jr. Editors; Humana Press, Clifton, N.J., 1991. This text is fully and completely incorporated herein by reference, word for word and paragraph for paragraph. The immunoassay-based evanescent sensors of the prior art do not utilize data collected continuously by the sensor over a time period to perform the assay. Rather a single point in time is defined for taking a single measurement from the sensor and a standard curve is prepared relating such single point measurements to concentration of antigen in the solution. The prior art is therefore directed toward assay of a specific compound in a sample rather than assessment of the kinetic and binding parameters describing the interaction between a component in the sample and a component attached to the sensor waveguide surface.

3. Background to the Evanescent Sensor Apparatus of the Invention

The essential feature of an evanescent biosensor, is confinement of the measurement area to the surface of the waveguide by taking advantage of the evanescent field associated with total internal reflection within the fiber. This was originally described in the context of immunoassay by Tomas Hirshfield in U.S. Pat. No. 4,447,546 entitled "Fluorescent immunoassay employing optical fiber in a capillary tube" which is herein incorporated by reference, line by line and word for word. The manner in which this functions is as follows.

Consider light incident at angle $\theta$ on the boundary between two optical media with indexes of refraction N and n (N>n). When the light is incident on the boundary at angles greater than or equal to the critical angle, $\theta_{crit}$ where $\sin(\theta_{crit})=n/N$, the light will be totally reflected from the surface. Although, light is not transmitted past the boundary and into the media with the lower index of refraction, electromagnetic theory shows that an evanescent electromagnetic field decays exponentially with perpendicular distance from the boundary. The characteristic 1/e depth of this decay for light of wavelength $\lambda$ incident at angle $\theta$ is given by the equation:

$$(\lambda/4\pi)(N^2 \sin^2 \theta - n^2)^{-1/2} \quad\quad \text{Equation 1}$$

This distance is large compared with the dimensions of proteins and biologically significant nucleotides. Thus, the light with wavelength $\lambda_1$ will interact with fluorescent molecules, which are associated with any proteins or nucleotides that are attached near the probe's surface, to generate fluorescence at wavelength $\lambda_2$. Because the waveguide is very large compared with the size of the proteins or nucleotides, a large fraction of the emitted fluorescence light at wavelength $\lambda_2$ will intersect the fiber optic sensor, then be trapped inside due to total internal reflection, and finally be carried back to a solid state light detector in the control unit.

Prior designs of evanescent sensor instruments achieve delivery of excitation light to and collection of fluorescence from the sensor fiber by means of free space propagation from a focusing lens into the fiber sensing element without the use of an intermediate low loss beam shaping means (U.S. Pat. No. 4,608,344, Method for the Determination of Species in Solution with an Optical Wave-Guide, Carter, J. N., Dahne, C. and Place, J. F.), (U.S. Pat. No. 4,447,546, Fluorescent Immunoassay Employing Optical Fiber in Capillary Tube, Hirschefeld, T. E.), (Publication: *Fluorometer and Tapered Fiber Optic Probes for Sensing in the Evanes-cent Wave,* by Golden, J. P., Shriver-Lake, L. C., Anderson, G. P., Thompson, R. B., Ligler, F. S., in *Optical Engineering,* July, 1997, p. 1458–1462). Shaping of the entering excitation light into an annular beam is described in U.S. patent application Ser. No. 08/616,576 entitled Surface Treatment and Light Injection Method and Apparatus which is assigned to the assignee of the present invention describes injection of annularized light at or near the critical angle. All methods of the prior art require that each sensor cartridge be manually aligned with the light from the focusing lens by adjustment means such as and without limitation to x,y,z stages upon which the sensor cartridge is mounted or adjustment of the focusing lens. This requirement is not well adapted for use of the instrument by untrained personnel. Prior art also does not provide a means for preventing side bands from a laser source of excitation light, from entering the sensor. Prior art is plagued by the problem that light is lost from the fiber sensor at any point of contact which has a higher refractive index than that of the sample. Efforts to deal with this problem are described in several patents. U.S. Pat. No. 4,447,546, Fluorescent Immunoassay Employing Optical Fiber in Capillary Tube, Hirschefeld, T. E., 1984, holds the fiber in place using a supporting stopper out of siloxane and coating the ends of the fiber with a low refractive index silicone. This doesn't fully solve the problems because the refractive index of silicones and siloxanes is at best 1.367. For a fiber in an aqueous solution having refractive index of 1.33, this creates an NA, of about 30.1°. Thus the light near the critical angle of 35.8° will be lost in the siloxane.

A method for dealing with this difficulty of light loss due to improper matching of NA, is found in U.S. Pat. No. 5,061,857, Waveguide-binding sensor for use with assays, R. Thompson, and C. Villarruel, 1991. Here the sensor fiber is tapered so as to produce a transformation of the effective NA of the fiber. The teaching under that patent requires that the fiber be etched in hydrofluoric acid to achieve correct tapering, which creates problems with respect to manufacturability.

A third method for avoiding light loss where the fiber contacts a support is described in U.S. Pat. No. 4,671,938, Immunoassay Apparatus, T. A. Cook, 1987. In this teaching, the sensor fiber is held at its distil end, but not at its proximal end, thereby avoiding the issue of contact with the supporting structure. The direct injection of annularized light at or near the critical angle could not be accomplished under this prior teaching because the nature of the teaching precludes inserting the proximal end of the sensor fiber into the coupling capillary containing the annularizing fiber.

All reported prior art describing evanescent sensors involves chemical sensitization of optical waveguides having surfaces from which all materials other than the core material of the optical waveguide have first been completely and thoroughly removed, usually by treatment with strong acid. Methods employed in prior art to protect these sensors from the sensitivity degradation caused by the non-specific binding of biological proteins to sensor surfaces, requires exposing said sensitized sensor surfaces to a solution of non-interfering proteins so that the non-interfering proteins bind to said sensor surfaces to prevent the subsequent binding of the interfering proteins. Because this method is never completely effective and non-specific binding severely degrades the attainable performance of sensors described in prior art. However, prior art indicates that enhanced protection of surfaces from biological proteins is possible by completely covering surfaces with protective coatings. For example, methods have been employed to protect surfaces from nonspecific binding to materials used in implantable devices such as catheters or materials for prostheses. In that context, the amorphous copolymers of tetrafluoroethylene and bis-2,2-trifluoromethyl-4.5-difluoro-1,2-dioxole sold under the trademark TEFLON AF® has been dissolved in a solvent containing fluorinated alkanes such as FLUORINERT®, and applied by deposition as a thin protective, totally enclosing layer to the surface of polymers in order to reduce thrombogenicity and complement activation. This is described in U.S. Pat. No. 5,356,668 by Duncan M. Paton, Timothy R. Ashton and Roshan Maini, 1994, entitled Fluorinating Polymer Surfaces.

U.S. patent application Ser. No. 08/616,576 entitled Surface Treatment and Light Injection Method and Apparatus which is assigned to the assignee of the present invention describes a method by which the nonspecific binding protection conferred by the copolymer of tetrafluoroethylene and bis-2,2-trifluoromethyl-4.5-difluoro-1,2-dioxole may be preserved, while still retaining a waveguide surface capable of chemical sensitization. A method is described therein showing a means to modify glass or silicon surface adhesion properties to substantially protect these surfaces from the non-specific binding of proteins by starting with a glass or silicon surface which has been coated with amorphous copolymers of tetrafluoroethylene and bis-2,2-trifluoromethyl-4.5-difluoro-1,2-dioxole, e.g. TEFLON AF® which have been baked onto the surface at temperatures near the copolymer's glass point so as to improve surface adhesion of the copolymers, and then using a solvent containing fluorinated alkanes such as FLUORINERT®, to substantially remove all of said coating material from said surface, except for nearly undetectable trace amounts of surface contamination from constituents from said cladding which are visible using atomic force microscopy as an open network of elevated regions surrounding the underlying clean, bare, glass or silicon surface regions. That patent application does not describe means by which said treatment may be applied to fibers in a batch process so as to produce optical waveguides of uniform quality.

This same coating material of amorphous copolymers of tetrafluoroethylene and bis-2,2-trifluoromethyl-4.5-difluoro-1,2-dioxole, e.g. TEFLON AF®, is applied to and baked on silica fibers for use as cladding on commercially available optical fibers which can be obtained from suppliers such as but not limited to Polymicro Technologies, Inc., 18019 N. 25th Ave., Phoenix, Ariz. 85023. However, in order for fiber having this cladding material to be used in an evanescentsensor, the said cladding must be removed from surface regions which will be chemically sensitized.

SUMMARY OF THE INVENTION

It is a first object of the present invention to provide an optical apparatus for use with an evanescent sensor.

It is a second object of the present invention to provide an apparatus which improves the utility of light sources (e.g. diode lasers or light emitting diodes) that have spectral features such as side-bands (both short and long wavelength) that would otherwise limit their applicability or diminish their performance in evanescent sensing instruments.

It is a third object of the present invention to provide an apparatus for containment of a sensitized optical fiber and a fluid to be tested, said apparatus being hereafter referred to as a fiber optic sensor cartridge.

It is an fourth object of the present invention to provide an apparatus for positioning a fiber optic sensor cartridge with respect to a coupling optical fiber, said coupling optical fiber being connected to an optical excitation means.

It is a fifth object of the present invention to provide a method and apparatus for monitoring binding between molecules of a specific protein type and a specific nucleotide sequence.

It is a sixth object of the present invention to provide a method and apparatus for assessing the functional competence of DNA-binding transcriptional regulators such as and without limitation p53 protein.

It is a seventh object of the present invention to provide a method and apparatus for evaluating the effects of a compound upon a biological system by monitoring the effect which said compound has on binding between a) molecules of a specific biological protein and molecules of a natural ligand for that protein, and b) binding between molecules of a specific biological protein and a nucleotide sequence resembling that of a nuclear response element through which said biological protein exerts its effects.

It is an eighth object of the present invention to provide a method and apparatus for measuring the binding of certain compounds to biological molecules which overcomes the various disadvantages of the prior art.

It is a ninth object of the present invention to provide a method which goes beyond the prior art in that it provides real-time description of binding between specific biological molecules and their ligands.

It is a tenth object of the present invention to provide a method which goes beyond the prior art in that it provides real-time data on binding between specific biological molecules and other molecular components which comprise a biological signal transduction mechanism.

It is an eleventh object of the present invention to provide a method and apparatus for assessing the type of impact (such as inhibitory impact or excitatory impact) on biological regulatory systems that a certain compound will be likely to exert.

It is a twelfth object of the present invention to provide a method which minimizes sensor to sensor response variation and which enables the manufacture of a multiplicity of identically and simultaneously processed and chemically sensitized fiber sensor elements which have a first non sensing region at one or both sensor ends created by surrounding the fiber with a chemically inert protective sheath means in which the interior layer of the protective sheath means has a low index of refraction, and a second sensing region created by processing the unclad fiber surfaces to create a fiber surface interspersed with a network of hydrophobic regions suitable for subsequent chemical sensitization.

The instrument of the present invention represents an improvement over the prior art of evanescent sensing in several regards. It describes a sensor cartridge which utilizes fibers created by means of a sensitization method wherein molecules of one component of a binding pair are bound to the longitudinal surface of an optical fiber between hydrophobic regions as taught by U.S. patent application Ser. No. 08/616,576, and assigned to the assignee of the present application, which text is fully and completely incorporated herein by reference, word for word and paragraph for paragraph. The sensor cartridge of the present invention represents an improvement upon the cartridge described in said patent application in that it is designed so as to be adapted for use with other improvements in the apparatus which are also described in the present invention.

The invention describes means by which light is shaped into an annular beam having a cone angle substantially at or near the critical angle of the fiber optic sensor, including means by which the angles of light included in the annulus are easily adjusted. This represents an improvement upon the annularizing apparatus described in the aforementioned U.S. patent application Ser. No. 08/616,576. The invention describes means by which said annular beam is delivered to the sensor cartridge with minimal loss, by means other than free space propagation from a focusing lens, which also represents an improvement upon the optical apparatus described in the aforementioned U.S. patent application Ser. No. 08/616,576.

The present invention addesses the problem of loss of light at contact points more effectively than the prior art as described in U.S. Pat. No. 4,447,546, and in a manner which doesn't require any alterations to the fiber core, and it offers clear advantages with respect to manufacturability over the prior art described in U.S. Pat. No. 5,061,857; which requires that the fiber be etched in hydrofluoric acid to achieve correct tapering so as to avoid such light losses. The present invention overcomes these difficulties by coating the longitudinal ends of the sensor fiber with a material having an index of refraction which is lower than that of the sample. The sensor fiber is directly butt coupled to an input fiber which is clad with material of similar refractive index. This allows annularized light at the optimum injection angle to be directly and efficiently coupled into the sensor fiber with minimal loss. The low refractive index coating also allows the fiber assembly to be supported by the fluid ferrules without light loss. The low refractive index coating utilized in the preferred embodiment of the present invention is amorphous copolymers of perfluoro (2,2-dimethyl-1,3 dioxole) and tetrafluoroethylene (e.g. Teflon AF®).

The invention also provides an apparatus for automatically aligning the sensor cartridge with the optical apparatus thereby providing simple, reproducible alignment of an optical fiber carrying excitation light with the fiber sensor cartridge. The present invention also utilizes an optical arrangement which prevents side bands, emitted by some laser light sources, such as and without limitation to diode lasers, from entering the optical fiber and degrading sensitivity. This problem is not addressed by the prior art.

The application to which this invention is applied also represents an innovation in that evanescent sensing fluorometry has not heretofore been applied to the study of binding between biologically significant nucleotide molecules and protein molecules, nor has it been applied to measurement of binding affinity and kinetics between receptor molecules and their ligands. Three specific embodiments are described in the present invention, representing novel applications of the technology. In the first example, measurement of binding between a nucleotide and a biological protein molecule is described. In the second, binding is monitored between a specific nucleotide and a specific biological molecule in a context where the effect of adding a ligand which binds to a different site in that biological molecule is of interest. A third embodiment describes a method by which an evanescent sensor apparatus can be used to determine the affinity of a biological molecule for its ligand.

The first preferred embodiment of the invention is exemplified by detection of the presence of ineffective mutations of the P53 protein by a fiber sensor possessing the nucleotide sequence of the nuclear response element for P53. The combination of the second and third preferred embodiments is exemplified using the human estrogen receptor. It permits assessment of both the affinity of a test compound for the receptor relative to the receptor's affinity for the nuclear response element, and assessment of the impact which binding of the test molecules by receptors has on the subsequent binding of receptors to the nuclear response element. These two pieces of information taken together provide a useful indication of the likely biological impact a test compound will have. This is relevant to evaluating compounds such as and without limitation, tamoxifen, which might be useful in treatment of hormone dependent cancers.

The invention accordingly comprises the apparatus possessing the construction, combination of elements and arrangement of parts, and the method comprising the several steps and relation and order of one or more of such steps with respect to the others, all of which are exemplified in the following detailed disclosure, and the scope of the application of which will be indicated in the claims.

DESCRIPTION OF FIGURES

Fuller understanding of the nature and objects of the present invention is obtained by reference to the following detailed description taken in connection with the accompanying drawings in which like numerals in said drawings denote like parts, and wherein.

DETAILED DESCRIPTION OF THE APPARATUS OF THE PREFERRED EMBODIMENTS OF THE INVENTION

Figure 1A:
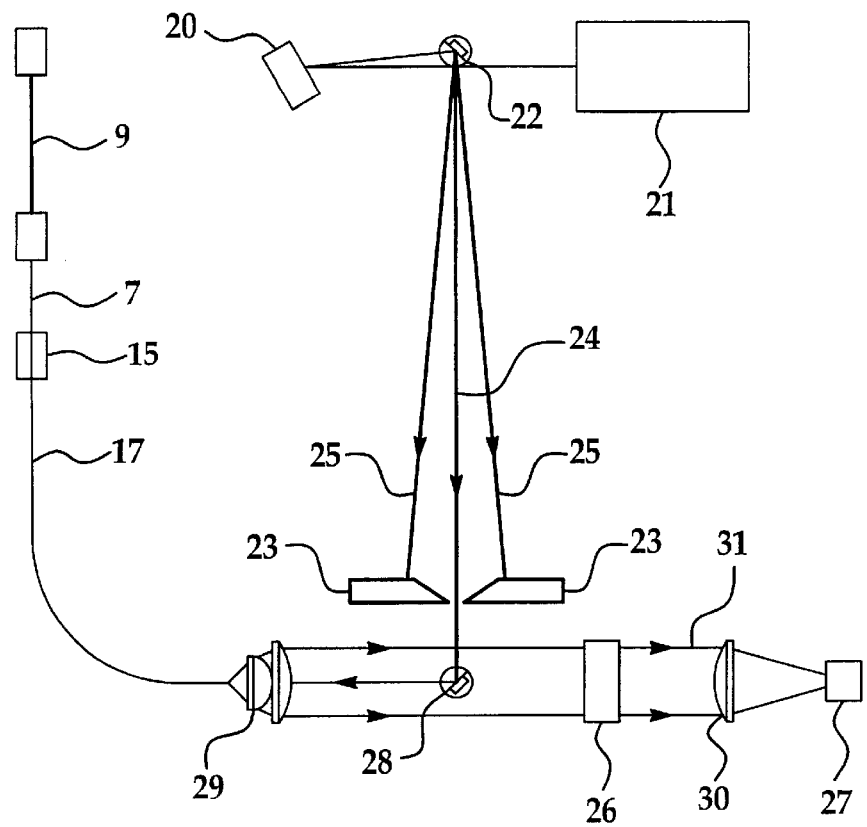
FIG. 1: Shows top and side views of the idealized optical apparatus of the invention, said apparatus having means for removing side bands from a laser source.
Figure 1B:
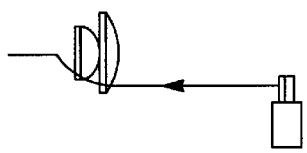

According to the first object of the present invention, an optical apparatus for use with an evanescent sensor is provided, and according to the second object of the present invention, said apparatus includes features which improve the utility of light sources (e.g. diode lasers or light emitting diodes) that have spectral features such as side-bands (both short and long wavelength) that would otherwise limit their applicability or diminish their performance in evanescent sensing instruments. Referring to FIG. 1, light from a light source (21), such as and without limitation, a laser diode, is directed to a dispersive element (20), such as and without limitation, a diffraction grating, situated such that light propagating from said light source impinges upon said dispersive element. In the preferred embodiment of this invention, said dispersive element comprises a diffraction grating in near Littrow configuration. Said impingent light, upon exiting from said dispersive element, thereafter propagates such that each constituent wavelength component of light is angularly dispersed as a function of wavelength. Said dispersive element functions to angularly separate unwanted wavelength band(s) from wanted wavelength band(s), and to direct all wavelengths to means (22) for directing said angularly dispersed light along a path of substantial distance, such as and without limitation a turning mirror. Said distance is substantial when the path length is sufficient to spatially separate unwanted wavelength band(s) (25) from wanted wavelength band(s) (24). Blocking element(s) (23) situated at said substantial distance to said dispersive element (20) intercept only unwanted wavelength band(s) (25). Selected wavelength band(s) (24) are not intercepted by said blocking element(s) (23), and thus, continue to propagate. Such an arrangement provides improvement over the prior art in that it yields a more complete separation between light generated by the excitation source and light generated from the binding of a solution component to the sensitized optical fiber. Without this feature, previous designs suffered from higher background readings resulting from propagation of laser side bands at wavelengths which pass through filter (26), reflecting back from the sensor (10) and being focused onto photodetector (27).

Said selected wavelength band(s) (24) of light are directed by means (28), such as and without limitation, a beam splitter, a prism or a partially reflective mirror, to pass off axis through focusing means (29) so as to enter the input face of annularizing optical fiber (17) as a narrow beam both off axis and at a specific injection angle to the optical axis so that the beam will first propagate as real skew modes in a substantially confined manner within the annularizing optical fiber (17), said skew modes uniformly distributing the light into a narrow annular band propagating at said specified angle within the annularizing optical fiber (17) and subsequently leaving the first annularizing fiber section and entering into a second fiber section (7) contained within the sensor cartridge (10), said fiber section having been sensitized to substantially react with test and reagent solution(s) only in the presence of a specific chemical. Said focusing means must possess an numerical aperture high enough to match that of annularizing fiber (17). In the preferred embodiments said focusing means comprises a high numerical aperture doublet, said doublet comprising a focusing meniscus lens and plano-convex collimating lens. Other focusing means may include elements such as and without limitation, a graded index lens, paraboloidal mirror elements or a holographic optical element. Annularizing fiber (17) provides means by which excitation light may be shaped to present light to the fiber sensor in the form of an annular ring at or near the critical angle of the sensor. While in one embodiment, a fiber sensor system using the previously described illumination system and incorporating an extended length of fiber preceding the sensitized fiber region could be used to produce a similar shaping of the light beam before it enters the sensitized region of the fiber, the preferred embodiment of the present invention utilizes a separate annularizing fiber (17) to provide a mechanism by which the shaping of the beam remains constant without requiring any adjustments of position as fiber cartridges are replaced. Fiber assembly (7) of sensor cartridge (10) is butt coupled to annularizing fiber (17) by means of coupling capillary (15). In the preferred embodiment, annularizing fiber (17) is a 400 μm fused silica multimode fiber clad with amorphous copolymers of perfluoro (2,2-dimethyl-1,3 dioxiole) and tetrafluoroethylene (e.g. Teflon AF®).

Excitation light passes through sensor cartridge (9) at angles at or near the critical angle, creating an evanescent field which excites fluorescent molecules which are bound to the surface of the sensor fiber. Fluorescence of unbound material is only very minimally excited by this evanescent field. Fluorescence from the molecules bound to said sensor fiber surface is evanescently emitted back into confined propagating modes of said sensor fiber, traveling back through coupling capillary (15), annularizing fiber (17), and focusing means (29). Light of wavelength at or near the excitation wavelength is blocked by band stop filter (26), while light of wavelengths corresponding to fluorescence of molecules bound to the surface of said sensor fiber passes through band stop filter (26) and is focused by means (30) into optical detector (27).

Figure 2A:
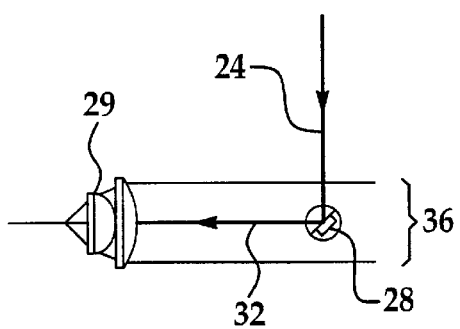
FIG. 2: Shows top and side views of the means of the invention for achieving an annularized excitation beam at or near the proper NA for the fiber in the medium of the sample.
Figure 2B:
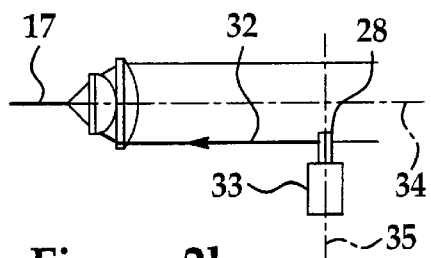

FIG. 2 provides an aid to understanding the manner by which the annular excitation beam of the desired angular distribution is created. An optical axis (34) is established by the position of an injection lens system (29) and an optical fiber (17) with its proximal end near the focal spot of said lens system. A light beam (24) is propagated to intersect the projected aperture (36) of said system on the side opposite from said optical fiber. In the preferred embodiment, said light beam propagates at an angle substantially perpendicular and skew to said optical axis. A redirecting axis is established (35), which is substantially perpendicular to the optical axis, about which a redirecting element (28) may rotate. The preferred embodiment has said redirecting axis intersect with said optical axis. Said redirecting element is positioned to intercept and redirect said light beam at an angle substantially parallel to said optical axis. Said redirecting element may be translated along said redirecting axis so that it protrudes into said projected aperture by an amount just sufficient to intercept said light beam, with all its mounting and manipulating apparatus (33) exterior to said projected aperture. Said light beam may be translated perpendicular to said redirecting axis by an external means, while maintaining interception by concomitant translation of the redirecting element, to affect a change in the perpendicular distance of said redirected beam (32) relative to said optical axis, thereby affecting the injection angle into said optical fiber. Embodiments of the redirecting element may be a mirror, a prism, holographic optical element (HOE), or any other means whereby the beam is redirected to the appropriate angle of parallelism to said optical axis from the transverse angle of said light beam.

Figure 3:
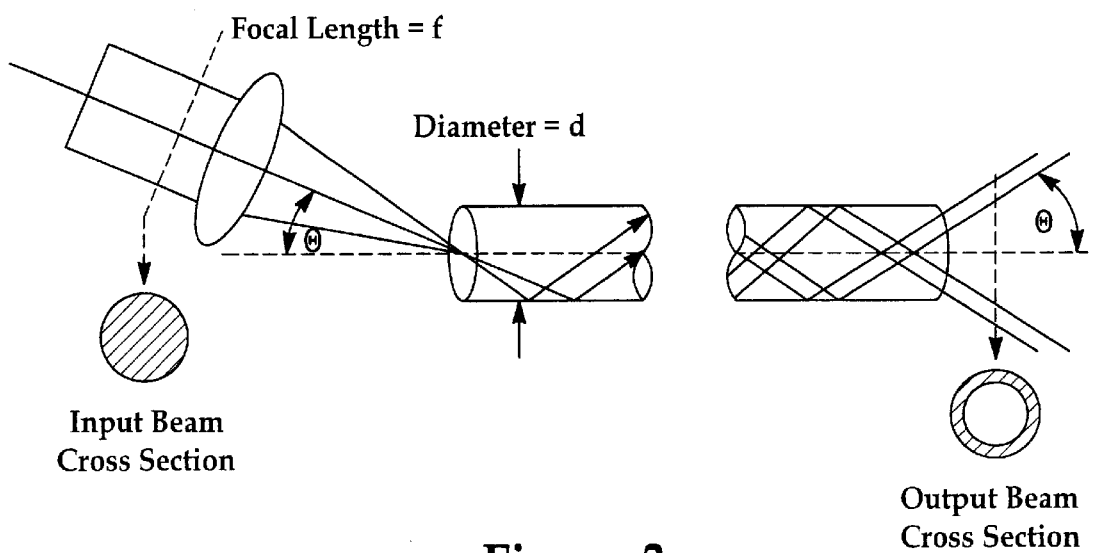
FIG. 3: Presents an idealized picture of annularization of a light beam within an optical fiber.

FIG. 3 presents an idealized picture of what happens to the ray bundle upon entering fiber (17) at angle θ Said parallel rays of light of said bundle have been focused by an optical element with focal length f into a section of optical fiber of diameter d. When this is done, the beam is forced to propagate through the fiber in high order off axis skew rays and is thus converted to an narrow annular cone with a half cone angle of θ at the output end of the fiber. In any plane perpendicular to the expanding cone, light radiation is concentrated in an annular ring whose thickness is determined by the initial spread in input angles induced by the focusing lens (i.e. determined by its numerical aperture (NA), f/#, or cone angle of the illumination lens) and by the area of inside of the fiber illuminated by the focused beam passing through the front face of the section of optical fiber. For example, as the injected beam diameter and the NA of the illumination objective are made smaller (e.g. NA<0.05), in the absence of other dispersive processes, the annular thickness or the emergent cone will become increasingly narrow and as a consequence, the angular distribution of rays which will be injected into and propagate within the sensor becomes narrowly peaked at close to the desired critical angle. On the other hand, as the NA of the illumination objective becomes larger (e.g. NA=0.3) or the diameter of the injected beam larger, the annulus will become thicker and because fewer of the ray angles emerging from the annularizer are close to the desired critical angle, the sensitivity of the evanescent fiber sensor will be reduced.

Figure 4B:
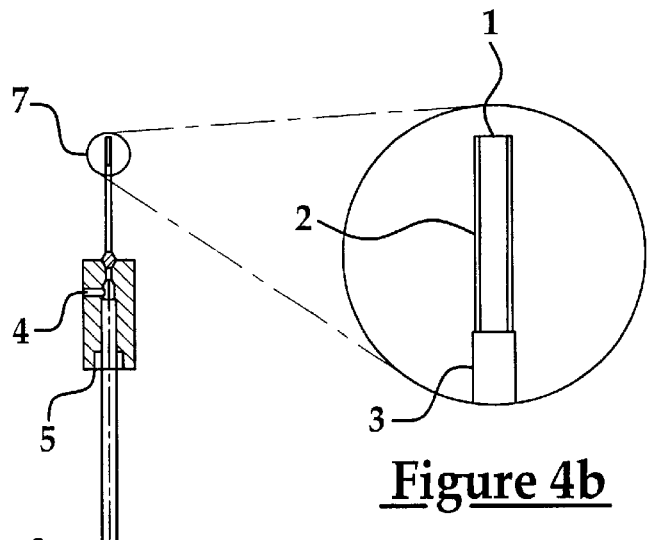
FIG. 4: Shows the sensor cartridge of this invention.
Figure 4A:
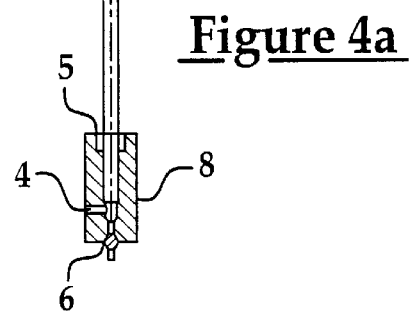

According to the third object of the present invention, an apparatus for containment of a sensitized optical fiber and a fluid to be tested is provided, said apparatus being hereafter referred to as a fiber optic sensor cartridge. FIG. 4 shows sensor cartridge (10) which is designed to receive said annular excitation beam and to propagate said beam with high efficiency so as to create an evanescent field along its length, said evanescent field exciting fluorescence in molecules which are bound to the surface of fiber assembly (7), and to receive said fluorescence which is evanescently emitted back into fiber assembly (7), and to propagate said fluorescence back to annularizing fiber (17).

Fluid ferrules (8) position fiber assembly (7) within a cylindrical tube of capillary dimensions (9) which allows fiber assembly (7) to be surrounded by the sample under test. The holes through which fiber assembly (7) passes through fluid ferrules (8) are sealed by means (6) such as and without limitation, 5 Minute® epoxy, to prevent leakage of sample. The cylindrical tube of capillary dimensions (9) is seated in fluid ferrules (8) by means, such as and without limitation, a captured O-ring (5) in a manner which prevents leaking of sample. The alignment of fiber assembly (7) and cylindrical tube (9) must be sufficiently centered with respect to one another along the longitudinal axis so as to prevent fiber assembly (7) from contacting cylindrical tube (9). Holes (4) allow sample to be brought into and out of cylindrical tube (9).

Fiber sensor assembly (7) is shown in the magnified section on the right of FIG. 4. At the center of fiber sensor assembly (7) is an optical fiber (1) which has been stripped of its cladding and which has been treated so as to possess a network of hydrophobic regions on its surface and which has been chemically sensitized so as to bind a specific type of molecule. Coating (2), having refractive index lower than that of the sample solution, is applied to the longitudinal surface at both ends of fiber (1) so as to constrain light within fiber (1) in the region where contact with other components occurs. Protective sheath (3), is made of a material which fits tightly around coating (2), and prevents mechanical abrasion of coating (2), such as and without limitation, polyimide tubing.

Figure 5:
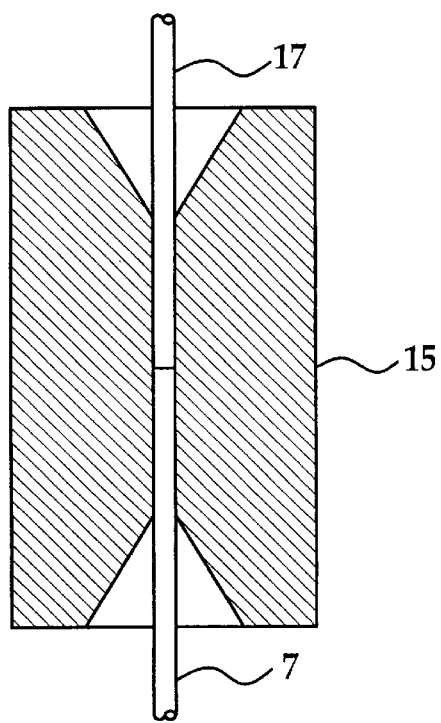
FIG. 5: Shows a front cross sectional view of the coupling capillary means by which the sensor cartridge of this invention is automatically alligned with and coupled to the annularizing fiber.
Figure 6:
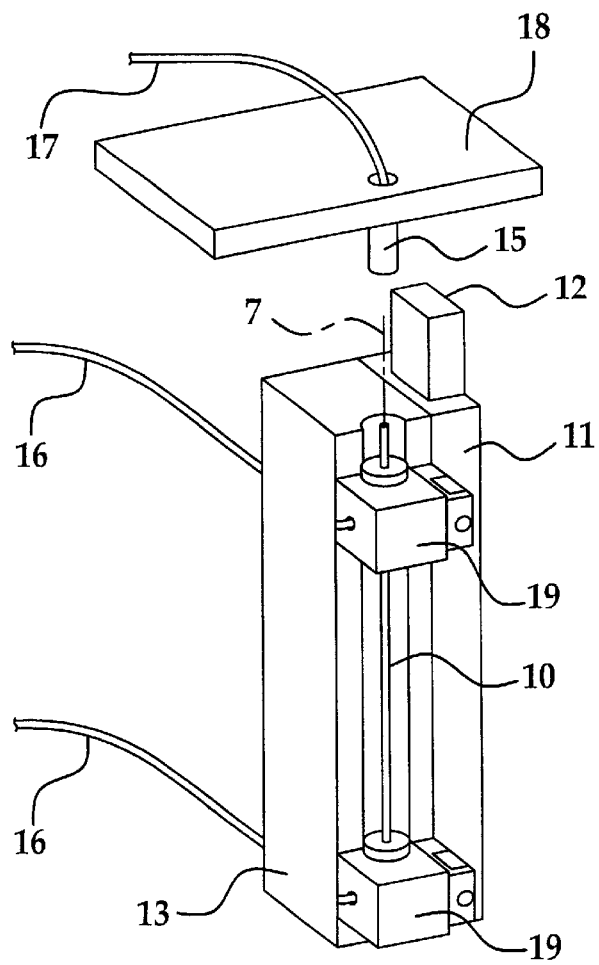
FIG. 6: Shows a positioning apparatus of this invention which provides a means by which the sensor cartridge is reliably brought into proper position in the coupling capillary.

According to a fourth object of the present invention, an apparatus for positioning a fiber optic sensor cartridge with respect to a coupling optical fiber, said coupling optical fiber being connected to an optical excitation means is provided. FIGS. 5 and 6 present the capillary coupler and the positioning apparatus which comprise this fourth object of the invention. With reference to FIG. 5, capillary coupler (15) provides means by which annularizing fiber (17) is butt coupled to fiber assembly (7) of sensor cartridge (10). In order to minimize loss of light at the point of coupling, said coating (2) should possess a refractive index which is essentially equivalent to that of the cladding of annularizing fiber (17). Fiber assembly (7) and annularizing fiber (17) easily enter capillary coupler (15) due to beveling of the entrance holes. The diameter of the inner bore of the coupler is such that said fibers are confined in all directions so that said fibers may be precisely mated by butt coupling. The material of the coupling capillary is non-abrasive in nature so that coating (2) is not scraped off of fiber assembly (7) during positioning in capillary coupler (15).

The sensor cartridge shown in FIG. 4 represents an improvement over the prior art in several regards. Because sensor fiber (1) possesses a network of hydrophobic regions on its surface, non-specific protein binding is greatly reduced, making the sensor less subject to fouling and interference from protein components of biological samples, as is taught in U.S. patent application Ser. No. 08/616,576 and assigned to the assignee of the present application.

A further improvement over prior art occurs because coating (2) provides a means of mounting the sensitized fiber within the sensor cartridge which minimizes loss of light at points of contact between the fiber and the supporting parts of the cartridge and the coupling capillary. The specific coating which is utilized in the preferred embodiments is amorphous copolymers of perfluoro (2,2-dimethyl-1,3 dioxole) and tetrafluoroethylene (e.g. Teflon AF™), which has a refractive index of approximately 1.31. Annularizing fiber (17) also is clad with amorphous copolymers of perfluoro (2,2-dimethyl-1,3 dioxole) and tetrafluoroethylene (e.g. Teflon AF™). Appreciation of this aspect of the invention requires an understanding of the role played by refractive index in evanescent sensing apparatus. The sine of the maximum external half cone angle at which light can be injected into an optical waveguide so as to propagate by total internal reflection within said optical fiber is known as the numerical aperture of the waveguide (NA). The first equation given below defines the relationship between the NA of the waveguide and the refractive indices its core and clad. The second equation relates the refractive indices of the waveguide and its surrounding medium to the maximum external angle of a light ray that will propagate under total internal reflection within the waveguide.

$$N.A. = (\eta^2_{core} - \eta^2_{clad})^{1/2} \qquad \text{Equation 2}$$

$$N.A. = \eta \sin \theta_{max} \qquad \text{Equation 3}$$

where $\eta = 1$ for air, $\eta_{core}$ = refractive index of the optical waveguide, $\eta_{clad}$ = refractive index of the material or sample surrounding the optical waveguide.

The refractive index of an aqueous sample is approximately 1.33. At the excitation wavelength used in the current embodiment, the refractive index of a fused silica optical fiber is approximately 1.456. From the above equation it can be calculated that light injected at a half cone angle of 36.3° will be totally internally reflected by the sensor fiber in an aqueous sample. Light at half cone angles greater than this will be lost from the fiber and enter the surrounding aqueous sample. The coating of refractive index 1.31 provides total internal reflection of light injected for angles less than a cone angle of 39.5°, thus an annular beam can be injected into a sensor fiber at angles at or near the critical angle for the sensor in an aqueous sample, without a loss of light. This makes possible the use of the capillary coupler shown in FIG. 5, wherein both the annularizing fiber and the sensor fiber are clad with amorphous copolymers of perfluoro (2,2-dimethyl-1,3 dioxole) and tetrafluoroethylene (e.g. Teflon AF™) to provide very low loss transfer of the light, annularized at optimum angle, to the sensor.

FIG. 6 describes means by which sensor cartridge (10) may be replaced and yet each cartridge is automatically brought into the correct position with respect to coupling capillary (15). Sensor cartridge (10) is essentially positioned between two V-blocks, the first being a V formed into the front surface of positioning apparatus body (13), and the second being carved into the rear surface of hinged support (19). Hinged support (19) is fastened to positioning apparatus body (13) in a manner permitting hinged support (19) to swing away from sensor cartridge (10) in order to replace said sensor cartridge. When closed, said hinged support is anchored shut by means of a clasp. Sensor cartridge (10) is placed in positioning apparatus body (13) in a manner which causes sample inlets (16) to be pressed into holes (4) of sensor cartridge (10) in a manner which prevents leaking of sample. Positioning apparatus body (13) is mounted on a translating component (11) which slides along track (12). Track (12) is mounted on the sensor housing, as is coupling capillary support (18), in a manner such that fiber assembly (7) is brought into coupling capillary (15) when positioning apparatus body (13) is translated along track (12) in the direction of capillary coupler (15). When fiber assembly (7) has been brought into contact with annularizing fiber (17) in coupling capillary (15), a screw is tightened to hold positioning apparatus body (13) in that location. To change cartridges, said screw is loosened, positioning apparatus body (13) is translated away from coupling capillary (15) along track (12), hinged support (19) is unclasped and opened and sensor cartridge (10) is replaced.

The foregoing description pertains to objects 1 through 4, and constitute the apparatus of the present invention. Objects 5 through 11 provide methods by which said apparatus and sensors may be used to achieve ends not previously described by the prior art of evanescent sensing fluorometry. Object 12 pertains to a method by which a multiplicity of sensor fibers may be simultaneously prepared so as to possess clean bare surface regions interspersed with a network of hydrophobic regions, said fibers being suitable for subsequent chemical sensitization and also being resistant to nonspecific binding by proteins. Objects 5–12 are described in detail, first as they apply to all specific embodiments and then in yet further detail as developed for certain preferred specific embodiments

PREFERRED EMBODIMENTS OF THE PRESENT INVENTION

General Apparatus and Methods of All Preferred Embodiments

Direct real time observation of binding between a certain nucleotide sequence and a certain protein is not currently part of the prior art of molecular biology or biochemistry. Binding between such molecules in typically measured by radiobinding assays requiring separation of bound from unbound components. According to the fifth object of the present invention, the following general method is provided whereby an evanescent sensing fluorometry apparatus such as and without limitation, the one which has been described in this patent, may be used to provide direct real time observation of binding between a certain nucleotide sequence and a certain protein.

Although the examples of preferred embodiments of the present inventions which are provided herein have utilized evanescent fiber optic sensors of the type described in objects 1–4 and 12 of the present invention, it is easy to visualize the possibility that the applications described in objects 5–11 could be carried out using other evanescent sensing apparatus such as and without limitation fiber optic sensors of other designs evanescent sensors utilizing waveguides of other geometries, such as a planar waveguide. All such applications of evanescent sensing instruments are considered to be within the objects and scope of objects 5–11 of the present invention. The apparatus and methods of objects 5–11 of the present invention are described in the most general case as being comprised of the following elements. Those elements having numbers ending in a (for apparatus) comprise the components of the apparatus of the present invention. Those elements having numbers ending in m (for method) comprise the steps of the method of the present invention.

1a: A quantity of optical waveguide pieces the number of which are determined by the number of sensors which are to be created, which have been cut to the size required from longer length of optical waveguide, and having been subsequently first processed to create clean bare surfaces or clean bare surface regions interspersed with a controlled surface density of a network of hydrophobic regions, and then having been treated so as to attach, directly or indirectly to the waveguide surface, a plurality of molecules or polymers which includes structural features conferring upon said molecules or polymers a binding affinity for a certain molecule of biological interest, are processed to create the sensor waveguide. This linkage may be accomplished either by adsorption of said molecules or polymers onto said exposed surface or by chemical reaction with a series of chemicals resulting in covalent bonding of said molecules or polymers to the exposed waveguide surface or by entrapment of said molecules within a polymer or gel matrix surrounding said optical waveguide. Item (7) of FIG. 4 comprises one embodiment of said optical waveguide, however it should be clear to those skilled in the art that any optical waveguide can provide the described function of component 1a in the context of the method herein provided and falls within the spirit and scope of the present invention.

2a: An optical apparatus which injects into said optical waveguide of component (1a), light at or near the critical angle for said waveguide in the sample medium, and measures the fluorescence, absorbance, luminescence or polarization of molecules at the waveguide surface while minimizing measurement the fluorescence, absorbance, luminescence or polarization of molecules in the surrounding solution which are not at the fiber surface. Such an apparatus is known to one skilled in the art as an evanescent sensing apparatus. One embodiment of said optical apparatus is described by the combination and arrangement of parts shown in FIG. 1, however it should be clear to those skilled in the art that any optical apparatus for which provides light at angles producing an evanescent field at the surface of said waveguide can provide the described function of component 2a in the context of the method herein provided and falls within the spirit and scope of the present invention.

3a: A sensor cartridge which enables the treated surface of the optical waveguide of component (1a) to contact test solutions. One embodiment of said sensor cartridge is shown in FIG. 4, however it should be clear to those skilled in the art that any sensor cartridge which contains said optical waveguide in a manner so that solutions may be contacted by said waveguide can serve the described function of component 3a in the context of the method herein provided and falls within the spirit and scope of the present invention.

4a: A means of positioning said sensor cartridge in said optical apparatus so as to enable excitation and measurement of fluorescence, absorbance or luminescence of molecules at the waveguide surface. The apparatus shown in FIGS. 5 and 6 comprises one embodiment of said positioning means, however it should be clear to those skilled in the art that any means of positioning said sensor cartridge so that light from said optical apparatus enters said waveguide so as to create an evanescent field at the surface of said waveguide and so that some characteristic of light from said sensor waveguide is measured, can serve the described function of component 4a in the context of the method herein provided and falls within the spirit and scope of the present invention.

5a: A means of acquiring data from the optical apparatus. Any means which can measure said characteristic of light from said waveguide and report said measurement along with the time said measurement was taken may comprise component 5a.

6a: At least one solution containing a plurality of said certain molecule of biological interest, said plurality of molecules having been tagged with molecules belonging to that class of chemicals which interact with light in a manner so as to alter the transmission of light by means such as and without limitation absorbance, fluorescence, luminescence, or polarization; or which produces a second chemical which interacts with light in said manner, such as and without limitation, an enzyme having action producing or destroying a fluorescent, absorbing, luminescent or polarizing compound. The molecular tag may be chemically attached to said plurality of molecules or it may be chemically attached to a molecule such as and without limitation, an antibody, having affinity for said certain molecule of biological interest. It is important that said certain molecule of biological interest be tagged in a manner which does not prevent the binding of said certain molecule of biological interest to said specific structural features of said optical waveguide.

When used according to the methods set forth in the present invention, said solution is diluted to yield two solutions, the first being such that it produces a small but reliable sensor response and the second being at a concentration at least 2 times that of the first, said second solution being of a concentration such that measurements may be made in the physiological concentration range of interest. Said first solution comprises a calibration standard and said second solution comprises a zero competition sample. In some embodiments, sample solutions having composition similar to that of said zero competition sample with the addition of a sample specimen, compound or collection of compounds which are to be tested are also created. It is important that the concentration of said calibration standard be low enough so that it not occupy a significant fraction of the available sites on the fiber by the end of the calibration run. Said diluted solutions are created in an assay diluent comprising buffering substances to maintain pH, ions as needed to create an ionic composition so as to optimize the stability and functioning of the biological molecules under study, protease inhibitors, proteins which reduce non-specific interactions and any other specific components needed to maintain the integrity of the biological molecules under study. If a nucleotide comprises either the specific feature on said waveguide or said biological molecule of interest, a plurality of molecules, such as and without limitation poly-deoxyinosine-deoxycytosine, will also be added so as to reduce nonspecific interactions with the nucleotide of interest.

7a: If the sensor apparatus being used produces scattering of light into the solution surrounding said waveguide, then two additional solutions are needed to establish a correction for signal due to such scatter, both being comprised of tagged molecules belonging to a class of chemicals which do not bind to the waveguide surface in assay diluent, said concentrations of tagged molecules in the two solutions being similar to the concentrations of tagged molecules in said calibration standard and zero competition sample.

The methods of objects 5–11 of the present invention have in common steps comprising:

1m: Said tagged binding molecules are combined with the sample on which the measurement is to be performed, and allowed to incubate for a time sufficient to achieve significant binding between said binding molecules and said protein in said sample. Whatever time is chosen, it must be held constant for all samples which are to be compared.

2m: The optical waveguide of component 1a is mounted in the sensor cartridge of component 3a and positioned in optical apparatus of component 2a, by means of positioning means of component 4a, such that light at or near the critical angle for the waveguide is focused and injected into the waveguide.

3m: If necessary, a solution containing a chemical which reduces nonspecific binding to the waveguide by the particular biological molecule of interest, is brought into contact with the sensor waveguide surface for a period sufficient to achieve requisite reduction of nonspecific binding.

4m: A measurement is taken on this solution using means of component 5a. This measurement comprises the quantity used in later calculations designated as "optical background." If background is very low in comparison to signal, this step may be eliminated.

5m: If the sensor apparatus being used produces scattering of light into the solution surrounding said waveguide, then the solutions of component 7a are brought into contact with the sensor waveguide surface and measurements are recorded by using means of component 5a. These measurements comprise the quantities which will be used in later calculations and designated as "calibration scatter background" and "sample scatter background." If scatter is very low in comparison to signal, this step may be eliminated.

6m: Said calibration standard of component 6a is brought into contact with the sensor waveguide surface and data comprising paired measurements of sensor output and time elapsed since the solution was first brought into contact with the sensor waveguide surface, is acquired using means of component 5a over a period sufficient to describe either or both (a) the initial rate at which said tagged plurality of a certain molecule of biological interest, binds to the waveguide surface and/or (b) the rate at which said tagged plurality of a certain molecule of biological interest, binds to said waveguide surface once a diffusion controlled rate is reached. If the particular composition of said calibration standard is such that bubbles tend to be caught in said sensor cartridge when solutions are changed, then sensor waveguide surface wettting enhancement means to reduce bubble formation such as and without limitation, ethanol or methanol, may be injected into said sensor cartridge both before and after said calibration standard is brought into contact with said sensor waveguide surface.

7m: Said calibration standard is removed from the sensor and said zero competition sample or one of said sample solutions of component 6a is brought into contact with the sensor waveguide surface and data comprising paired measurements of sensor output and time elapsed since the solutions was first brought into contact with the sensor waveguide surface, is acquired using means of component 5a using a timing paradigm identical to that used in said step 6m.

8m: If an actual affinity constant is desired for binding between said biological molecule of interest and said specific binding feature of said optical waveguide, following data acquisition from said fiber surrounded by said sample, said sample is removed and said assay diluent containing no tagged molecules, is injected into said sensor cartridge and data is similarly acquired as said tagged biological molecule of interest is released from binding to the fiber. This measurement, provides the off rate for binding, and typically takes significantly longer than the initial measurement, which provides the on rate of binding.

9m: The real time data describing the binding between said certain biological molecule of interest and said specific binding feature on said optical waveguide is processed in different ways, depending upon the desired outcome. A procedure is provided whereby the binding activity of a sample relative to a calibration solution is calculated. According to the eighth object of the present invention, additional methods of data treatment are provided under the detailed description of for the calculation of an affinity constant for binding between said certain biological molecule of interest and said specific binding feature of said optical waveguide and for calculating the net binding constant when said certain biological molecule exhibits co-operative binding.

Procedure for Determining Relative Sample Binding Activity (S/C)

Binding activity, is often the quantity of interest in comparing biological samples, or in assessing the effect of a compound upon a biological sample. Rather than resembling an immunoassay, which yields a concentration of an analyte in a sample, this procedure provides a value for a quantity designated (S/C) which a represents the product of the concentration of said biological molecule of interest in the sample and the affinity constant between said biological molecule of interest and said specific binding feature of said optical waveguide. The quantity "S/C" addresses the question of biological effectiveness of the molecules under investigation. Related concepts are familiar to those skilled in the art of biochemistry as they pertain to enzymes and peptide hormones. The methods of the invention normalize the activity to that of a known standard, said standard being present in said calibration standard of component 6a. The procedure for determining 'S/C' comprises the following steps in combination:

1. If step 5m was necessary, then subtract said calibration scatter background from all data obtained in step 6m. If step 5m was unnecessary, then subtract said optical background from all data obtained in step 6m.
2. If step 5m was necessary, then subtract said sample scatter background from all data obtained in step 7m. If step 5m was unnecessary, then subtract said optical background from all data obtained in step 7m.
3. Divide the results of step 2 by those of step 1 for each point.
4. Graph the outcome of step 3 on the y-axis versus on the x-axis, the amount of time which has elapsed since solutions were brought into contact with the sensor waveguide surface. This will result in a graph which will change rapidly during the period of initial binding, but will settle to a more or less horizontal straight line once the diffusion controlled period of data acquisition is reached.
5. Average the y values over at least 6 of the last data points in the straight line region of the graphs obtained in step 4. The quantity derived in said fashion is hereafter referred to as "S/C." A normal range for S/C is established and used to identify samples which exhibit atypical sample activity. If it is reasonable to assume that $K_\alpha$ for the sample and for the calibration standard are identical, then S/C is equal to the concentration of said biological molecule of interest in the sample divided by the concentration of the concentration of said biological molecule of interest in the calibration standard. If said calibration standard is created so as to have a known concentration, then the concentration of the said biological molecule of interest in the sample can be calculated by multiplying the quantity S/C by the concentration of said calibration standard.

Specific Means of the Specific Objects of the Present Invention

According to the fifth object of the present invention, a method and apparatus are provided for monitoring binding between molecules of a specific protein type and a specific nucleotide sequence.

In component 1a, said features conferring upon said molecules or polymers a binding affinity for a certain molecule of biological interest of comprises a specific nucleotide sequence, and certain molecule of biological interest comprises a protein or portion thereof, said protein or portion thereof also comprising said certain molecule of biological interest in component 6a. Also according to the fifth object of the present invention, in component 1a, said features conferring upon said molecules or polymers a binding affinity for a certain molecule of biological interest of comprises a protein or portion thereof, and said certain molecule of biological interest comprises a specific nucleotide sequence, said specific nucleotide sequence also comprising said certain molecule of biological interest in component 6a.

According to the sixth object of the present invention, a method and apparatus are provided for assessing the functional competence of DNA-binding transcriptional regulators such as and without limitation, p53 protein. This is achieved by application of the method of the fifth object of the invention specifically to measurement in a biological sample of binding between a plurality of DNA-binding transcriptional regulator molecules and and a plurality of the nucleotide to which said DNA-binding transcriptional regulator binds. In the case of the p53 protein, in component 1a, said features conferring upon said molecules or polymers a binding affinity for a certain molecule of biological interest of comprises the nucleotide sequence to which the p53 protein binds in order to regulate transcription of the p21 protein, and certain molecule of biological interest comprises p53 protein in a biological sample, said p53 protein in said sample having been tagged by means of an antibody to which has been coupled molecular tags of a type described in component 6a. Such an application of the invention provides a means of screening biological samples to identify those from individuals possessing a p53 mutation. Such a mutation causes the individual to be much more prone to developing cancer.

According to the seventh object of the present invention, real time data acquisition occurs when said evanescent sensing apparatus created by components 1a–7a utilizes as component 5a an automated means of computer controlled data acquisition employing a timing paradigm which is rapid enough to capture the measurable changes in signal. Typically this is on the order of 2–4 seconds between data points.

According to the eighth object of the present invention, a procedure is provided for processing data obtained using the described apparatus and method to yield an affinity constant for binding between said biological molecule of interest and said specific binding feature of said optical waveguide.

Procedure for Determining an Affinity Constant

Said affinity constant is calculated from the equations:

$$K_a = k_{on}/k_{off} \quad \text{Equation 4}$$

For first order kinetics, $k_{on}$ is a function of concentration of said protein in said sample ([P]) and effective concentration of said molecules, ([N]) on said fiber: This equation pertains to the initial rate of binding.

$$\text{signal at time } (t) = k_{on} \epsilon \log [P][N] \quad \text{Equation 5}$$

where
- $k_{on}$ and $k_{off}$ are both derived from real time data obtained,
- $\epsilon$ = a constant which relates the signal read by the sensor to the moles of tagged molecules bound to the surface of the sensor fiber.
- [P] = the concentration of said certain molecules of biological interest,
- [N] = the concentration of said binding molecules on said sensor fiber.

Equations of a similar type pertaining to second or third order kinetics, as may be found in any text on physical biochemistry, may be substituted as is appropriate.

Once data has been automatically acquired, affinity constants may be calculated from equations 4 and 5 using known concentrations of said certain molecule of biological interest in place of [P] in equation 5. The value of the factor $\epsilon$, which converts the sensor reading to a molar concentration of said tagged certain molecules of biological interest can be determined by performing the steps which give the S/C value for a single solution containing no competing ligand. Said solution is then removed and used a second time in a second sensor in exactly the same manner. The concentration of said tagged certain molecules of biological interest calculated from the S/C value obtained with the second sensor is then subtracted from the concentration of said tagged certain molecules of biological interest calculated from the S/C value obtained with the first sensor. The moles of said tagged certain molecules of biological interest which would have to be removed from the solution to result in this concentration change for the volume of liquid contained in the sensor correspond to the moles of said tagged certain molecules of biological interest on the first sensor fiber. Division of the final reading from the first fiber sensor by the moles of said tagged certain molecules of biological interest on the first sensor fiber provides the factor, $\epsilon$.

The $K_d$ for binding between unliganded said certain specific molecules of biological interest, such as and without limitation a biological receptor protein and the subsequent molecular component of a signal transduction pathway such as and without limitation, a DNA molecule, is calculated using equation 6. The derivation is carried out in terms where said certain specific molecules of biological interest comprises a biological receptor, R.

$$K_d = k_{off}/k_{on} = [L_S][R]/[RL_S] \quad \text{Equation 6}$$

where
- $K_d$ = The dissociation constant between the sensor and the waveguide.
- $k_{off}$ = The initial slope of the line obtained by plotting the sensor output obtained in step 8m when the solution of component 6a contains none of the test compound (the zero point for the series of test solutions) versus time. Said slope is then multiplied by a factor describing the number of moles of tagged receptor bound to the sensor per unit of sensor output.
- $k_{on}$ = The initial slope of the line obtained by plotting the sensor output obtained in step 8m when the solution of component 6a contains none of the test compound (the zero point for the series of test solutions) versus time and multiplying said slope by a factor describing the number of moles of tagged receptor bound to the sensor per unit of sensor output.
- $L_S$ = The concentration on the waveguide surface of the molecular feature which acts as a binding ligand for the receptor.
- R = The concentration of unbound receptor in the solution.
- $RL_S$ = The concentration of receptor bound to the waveguide surface. This is the measured signal generated by the sensor multiplied by a factor describing the number of moles of tagged receptor bound to the sensor per unit of sensor output.

The relationship between the concentration of receptor added to the solution that which is bound is expressed by Equation 7.

$$[R_{total}] = [R] + [RL_2] \quad \text{Equation 7}$$

Combining Equations 6 and 7 provides a form from which a meaningful data plot can be derived.

$$K_d = k_{off}/k_{on} = [L_S][R_{total} - [RL_2]]/[RL_S] \quad \text{Equation 8}$$

The value of $k_{on}$ is calculated using the starting value of:
$R_{total}$ = the concentration of receptor initially placed in the solution, and $[RL_S] = 0$.

The value of $k_{off}$ is calculated using the starting value of:
$R_{total} = 0$ concentration of receptor initially placed in the solution, and
$RL_S$ = (sensor reading just when buffer was added)×(factor to convert sensor reading to molar concentration of $[RL_S]$).

$[L_S]$ is determined by allowing a fiber to incubate with an excess of tagged receptor until the signal from the sensor no longer rises. That value is then multiplied by the factor which converts sensor reading to molar concentration of $[RL_S]$.

Also according to the eighth object of the present invention, biological molecules displaying cooperative binding of ligands may be investigated by a unique method of the present invention. This method overcomes the disadvantages of the prior art in that it does not require radioactive labels and it does not require that an equilibrium condition be reached prior to measurement. Fiber optic sensors which are configured for operation in competitive assay offer a convenient method for study of cooperativity in binding. Binding of one molecule of ligand to a macromolecules displaying cooperativity increases the affinity constant of the macromolecule for binding of the second ligand. In the case of a fiber optic sensor in which ligand is on the fiber, this gives rise to an unusual profile for a competition curve. Under conditions of non-cooperativity, the initial uncompeted reading from the fiber sensor is the highest reading. Each increasing amount of competitor brings a decreasing fiber sensor response. However, if cooperativity is present, the competition curve rises in response to very low concentrations of competitor, reaching a peak response at some concentration and then dropping as the concentration of competitor continues to increase. The mathematics and forms relating in general to cooperative binding are thoroughly described in the book *Physical Biochemistry, Applications to Biochemistry and Molecular Biology* by David Freifelder; W. H. Freeman and Co., New York; 1982, p 655–684. This text is fully and completely incorporated herein by reference, word for word and paragraph for paragraph.

A Method for Determining Binding Constants for Receptors Exhibiting Co-operative Binding According to the method of the present invention, the specific binding feature of the optical waveguide of component 1a is a plurality of molecules which act as a ligand for said certain molecules of biological interest. Calibration solutions of component 6a comprise a low concentration of tagged said certain molecules of biological interest, said calibration solutions being essentially identical for all samples. Several standard sample solutions of component 6a are created, each comprising a fixed higher concentration of tagged said certain biological molecules to which has been added one of a series of specific concentrations of a ligand of known binding affinity (Ligand A). Additionally, a series of several test sample solutions are created, the concentrations of ligand (Ligand B) in said test samples being identical to those of Ligand A in said series of standard samples. All solutions are tested using identical protocols according to the method comprising steps 1m–7m of the present invention. It is important that the experiment be conducted in a manner such that the time between addition of the sample ligand to the solution containing the molecules of biological interest be the same for all test solutions of both Ligand A and Ligand B.

For solutions containing a test compound which binds to said certain specific biological molecules of interest in a way which induces cooperativity, certain low concentrations of the test compound will produce a quantity S/C from step 9m which is higher than the theoretical ratio. As the concentration of test compound is increased, the quantity S/C will drop from the increased value seen at low concentrations, finally falling below the theoretical ratio and continuing to drop until saturation is reached. If the test compound binds to said certain molecules of biological interest in a way which does not induce cooperativity, the quantity S/C will drop below the theoretical ratio even at low concentrations and continue the drop as the concentration of test compound increases until saturation is reached.

This method provides a simple direct means for quickly determining (1) whether the test compound binds to said molecules of biological interest, and (2) whether the test compound binds in a manner so as to induce cooperative binding between said certain molecules of biological interest and additional ligands. When said certain molecules of biological interest is a biological receptor, since receptor binding is the first step in affecting biological regulatory mechanisms, this simple procedure provides a method for rapidly screening samples to detect the presence of compounds having potential to disrupt certain biological control mechanisms involving the biological receptor used in testing. This type of screening is particularly well suited to testing environmental samples.

In order to enable calculation of the effective binding constant ($K_R$) between a certain test compound and said certain specific biological molecules of interest, a method is presented for calculating that constant relative to that of a compound having a known effective binding constant for said certain specific biological molecules of interest. Said effective dissociation constants represent the net effect of two different dissociation constants in molecules exhibiting cooperative binding.

$$\frac{K'_R}{K_R}[L_s] = [L] \qquad \text{Equation 9}$$

where $K'_R$=The known binding constant between a specific ligand and said certain specific biological molecules of interest $K_R$=The unknown binding constant between a certain test compound and said certain specific biological molecules of interest, the known binding constant between a specific ligand and said certain specific biological molecules of interest, $[L_s]$=The concentration of the test compound at which the peak signal occurs, and $[L]$=The concentration of the known ligand at which the peak signal occurs.

By first running a fiber sensor with said standard sample solutions containing ligand having a known $K'_R$ for said certain specific biological molecules of interest, the quantity $K'_R$ can be calculated from the concentration at which the peak reading occurs. This $K'_R$ can then be used with data from said test sample solutions containing a series of concentrations of ligand of unknown $K_R$ to determine the $K_R$ of that ligand for the receptor.

Thus the $K'_R$ for the test compound can be calculated from sensor data and knowledge of the $K'_R$ for the known ligand.

The mathematical basis for data treatment utilizing equation 5 is herein described in terms where said biological molecule is a receptor having concentration [R]. If the competitor is incubated with the receptor prior to injection into the fiber sensor, the situation prior to injection is described in terms of variables typically employed in a Hill plot for determining cooperativity by the equations $$\frac{v}{n-v} = K_T[L] \text{ as } [L] \text{ approaches } 0,$$

and $$\frac{v}{n-v} = K_R[L] \text{ as } [L] \text{ approaches } \infty$$

Where v=Total number of occupied ligand sites.

n=Total number of ligand site.

$K_T$=Microscopic binding constant for unliganded receptor.

$K_R$=Microscopic binding constant for monoliganded receptor.

[L]=Concentration of competitor in solution.

Upon injection, the binding of the ligand on the fiber to the receptor is described by the equations given below. If $K_R > K_T$, then as [L] increases, $[RL_S]$ increases until the biliganded dominates the following equations:

$$[RL_S] = L_S (K'_T [R_0] + K'_R [R_1])$$

$$[R_T] = [R_0] + [R_1] + [R_2]$$

$$[R_1] = K_T [R_0][L]$$

$$[R_2] = K_R [R_1][L] = K_T K_R [R_0][L]^2$$

Where

[RL$_S$]=receptor bound to fiber.

[L]=concentration of ligand in the solution.

[L$_S$]=concentration of ligand on the fiber.

[R$_T$]=Total concentration of receptor.

[R$_0$]=concentration of unliganded receptor in solution after incubation with competitor.

[R$_1$]=concentration of monoliganded receptor in solution after incubation with competitor.

[R$_2$]=concentration of biliganded receptor in solution after incubation with competitor.

K'$_T$=microscopic binding constant between fiber ligand and unliganded receptor.

K'$_R$=microscopic binding constant between fiber ligand and monoliganded receptor.

The measurable signal from the fiber optic sensor is proportional to [RL$_S$]. For positive cooperativity, $k_R > k_T$. Consequently, by the time the peak signal is reached, [R$_1$] is sufficiently greater than [R$_0$] so that the latter can be ignored. As [L] is increased, the condition at which the peak signal occurs is described by:

$$K'_R [L_S][R_1] = [R_2] = K_R [L][R_1]$$

This can be rearranged to predict the concentration at which the peak will occur.

$$\frac{K'_R}{K_R}[L_s] = [L] \quad \text{Equation 10}$$

Although the foregoing equations are descriptions of equilibrium conditions, their validity for application to non equilibrium data obtained from fiber optic sensors derives from the observation that for first order kinetics, t, the time interval required for obtaining any given extent of binding, x, is given by the equation:

$$\tau = \frac{1}{k}\ln\frac{1}{1-x}$$

where k is the kinetic constant for the binding.

Thus, as long as the time the test ligand and the biomolecule are in contact, and the precise moment of introduction of sample mixture into the fiber sensor remain constant, the above mathematical derivation applies because comparisons are always carried out at a time corresponding to the same fractional extent of equilibrium binding.

According to the ninth object of the present invention, the methods of objects 5–8 are applied to investigation of binding between biological molecules which play a crucial role in transduction of a signal initiated by the binding of a ligand to a biological macromolecule such as and without limitation, binding of a receptor to its nuclear response element in response to binding of the receptor to a steroid.

According to the tenth object of the present invention, the method described in the fifth object of the invention is carried out on a sample using a sensor cartridge possessing a fiber which has been chemically treated so as to attach, directly or indirectly to the longitudinal fiber surface, a plurality of molecules possessing a specific nucleotide sequence similar to that of the nuclear response element for said specific biological protein. A plurality of the biological protein of interest is tagged, either directly, or indirectly through antibodies to said biological protein, with a chemical belonging to that class of chemicals which interact with light in a manner so as to alter the transmission of light by means such as and without limitation absorbance, fluorescence, luminescence, or polarization. Standards and samples are diluted into an assay buffer comprising molecules which will reduce nonspecific binding to DNA, such as and without limitation polydeoxy inosine-deoxycytosin, buffering substances for maintaining pH, ions and protease inhibitors and any other specific components needed to maintain the integrity of said specific biological protein. Calibration standard solutions comprising a low level of said biological protein, are used in the manner of the fifth object of the invention. Test sample solutions comprise a concentration of said biological protein, said concentration being held constant and being set to approximate the concentration of said biological protein in vivo, and also comprising a concentration of the compound to be tested. Several test samples having different concentrations of a given compound are compared with a similar test sample having no test compound present according to procedures described in the fifth object of the present invention. The impact which the test compound at a given concentration, has upon binding between said biological protein and said nuclear response element may be assessed by comparing the value of S/C for the sample without test compound with that of the sample containing a given concentration of the test compound.

Evaluation of the impact of said test compound upon binding between said specific biological protein and its natural ligand is achieved in a similar manner using a sensor cartridge having a fiber which has been chemically treated so as to attach, directly or indirectly to the longitudinal fiber surface, a plurality of molecules of said natural ligand. As before the impact of the test compound is reflected by changes in S/C as compared to that of a sample without said test compound.

According to the eleventh object of the present invention, the method of the tenth object of the present invention is applied. With reference to sensor fibers having attached nucleotide sequence of said nuclear response element, if S/C for test samples is equal to or lower than S/C for a sample containing no test compound, and if with reference to sensor fibers having attached ligand, S/C is also lower, then the test compound is inhibitory. With reference to sensor fibers having attached nucleotide sequence of said nuclear response element, if S/C for test samples is higher than that of a sample containing no test compound, then the test compound is excitatory. If S/C remains constant for both fiber types, then the test compound is neither excitatory nor inhibitory.

According to the twelfth object of the present invention a method is provided which minimizes sensor to sensor response variation and which enables the manufacture of a multiplicity of identically and simultaneously processed and chemically sensitized fiber sensor elements which have a first non-sensing region at one or both sensor ends created by surrounding the fiber with a chemically inert protective sheath means in which the interior layer of the protective sheath means has a low index of refraction, and a second sensing region created by processing the unclad fiber surfaces to create a fiber surface interspersed with a network of hydrophobic regions suitable for subsequent chemical sensitization. It is the purpose of the network of hydrophobic regions to prevent large molecules such as proteins, from reaching the waveguide surface while permitting access to the waveguide surface to smaller molecules such as and without limitation, silanes and heterobifunctional cross-linking molecules. This provides protection from non-specific binding by proteins while preserving capacity for chemical sensitization. The method of preparing the optical fiber (1) for chemical sensitization is as follows. Optical fiber manufactured with a low index coating (2) such as and without limitation, amorphous copolymers of perfluoro (2,2-dimethyl-1,3 dioxole) and tetrafluoroethylene (e.g. Teflon AF™) is obtained from the manufacturer. From this fiber, sections of the proper length are obtained using an appropriate method such as, but without limitation, by cleaving. The inert protective sheath (3) is then hermetically sealed around each fiber end to prevent subsequent chemical processing steps from removing the low index coating (2) beneath the sheathing. Means of hermetically sealing the sheathing to the fiber include, but are not limited to, heat shrinking the sheathing material to the low index coating (2) surface. The sheathed fibers are then cleaned using solvent washes, and/or ultrasonic cleaning to remove residual surface contamination and are placed in a carrier means capable of simultaneously holding a multiplicity of fibers during the chemical sensitization process to follow. This carrier means ensures that fiber surfaces are not touched except at the unsensitized sheath ends (3) and allows solvents and sensitizing chemicals to freely circulate in the regions surrounding the unsheathed fiber surfaces. This carrier means also ensures that the multiplicity of senor fibers prepared as a single batch in this manner will have a common chemical response to the analyte they will be used to measure.

To prepare the network of hydrophobic regions on said fiber surface, a solvent capable of removing the low index coating is then placed in the carrier. The protective sheaths prevent the solvent from removing the low index coating beneath the sheathing while allowing most of the low index coating material to be removed from the fiber surface. For fibers coated with amorphous copolymers of perfluoro (2,2-dimethyl-1,3 dioxole) and tetrafluoro-ethylene, a polyfluorinated solvent such as, but without limitation to, Fluorinert™ from the 3M Corporation. At the proper time, such as and without limitation, 30 minutes, solvent is removed and the fibers dried, whereupon the exposed fiber surfaces are found to possess a residue of hydrophobic regions which can be visualized using atomic force microscopy but which are otherwise invisible using optical microscopy. By adjusting the timing of this step, the surface density of these hydrophobic regions may be controlled. After the hydrophobic regions are created on the fiber surfaces, the fibers may be chemically sensitized within the carrier in a plurality of methods, including, but not limited to those described in the preferred embodiments of the present invention. The presence of the hydrophobic regions greatly reduces nonspecific binding of protein to the fiber because large molecules cannot get to the surface of the fiber, while small molecules such as silanes which may be used to sensitize the fibers can get to the surface.

EXAMPLES OF THE PREFERRED EMBODIMENTS OF THE PRESENT INVENTION

First Example

The first example of a preferred embodiment of the present invention is a fiber optic sensor having components and method adapted to identify the presence of estrogen mimics in a liquid sample; and to perform measurements from which may be calculated the effective $K_d$ of the estrogen mimic in the sample for recombinant human estrogen receptor; and to assess the effect of said estrogen mimic on biological response through estrogenic signal transduction mechanisms. To these ends, components of an evanescent fiber optic sensor were constructed as described below. Component 1a takes two forms, type 1 which provides a surface possessing features which resembles the estrogenic compound estrone-3-glucuronide, and type 2 which provides a surface feature which resembles the nuclear response element which binds human estrogen receptor in vivo. Type 1 fibers are used to obtain information leading to calculation of the effective $K_d$ of the estrogen mimic in the sample for recombinant human estrogen receptor. Type 2 fibers provide quantification of the binding of the estrogen receptor to its nuclear response element in the presence and absence of sample being tested. They are used to assess the impact of the sample on the biological response through estrogenic signal transduction mechanisms.

To further understand the present invention as it relates to the first example of a preferred embodiment, details first of the components and then of method of utilization follow.
Component 1a Type 1: Preparing Optical Fibers Having Estrone-3-Glucuronide Surface Features 400 $\mu$m step indexed, multi-mode, fused silica fiber clad with amorphous copolymers of perfluoro (2,2-dimethyl-1,3 dioxole) and tetrafluoroethylene (e.g. Teflon AF™), Product #FSU400 420, was obtained from Polymicro Technologies Inc., 18019 N. 25th Ave., Phoenix, Ariz., 85023-1200. Fiber was cleaved using a York Electronic Fiber Cleaver to yield 10 cm pieces with optically acceptable end faces. Pieces were cleaned by sonication in methanol for 30 minutes and the end cladding was protected by covering one end with a 1 cm and the other end with a 1.5 cm piece of #25 black polyimide tubing, 0.002 wall, (from HV Technologies, Inc., P.O. Box 948, Trenton, Ga. 30752) and heat shrinking the tubing so that it seals itself around the cladding. This protects the cladding from being dissolved away by subsequent chemical procedures. The refractive index of this cladding prevents light from leaking out of the fiber where the fiber contacts the sensor cartridge ends. It is therefore important that the cladding be protected on the parts of the fiber which will contact other sensor components. A quantity of fibers (up to 64 at a time) was then placed in a carrier which holds the fibers vertically in a reservoir so that fibers were surrounded by chemicals which were injected and removed using a syringe. The carrier comprised a solid cylindrical core of material which is not dissolved in any of the solvents used during the cladding removing or sensitization of the fibers. Both ends of the core were affixed to a disc having 64 holes of a size so as to permit optical fibers to pass through said holes, said holes being roughly 0.08" from the edge of said discs. The holes in the disc affixed to the bottom of said cylindrical core were blind so that after fibers pass through said holes on the upper disc, said fibers rested ,in the holes of said lower disc. Said carrier fits into a cylindrical reservoir having a fluid access port through which reagents and drying gases may enter and leave said reservoir. The reservoir was filled with a fluid capable of slowly dissolving off the cladding of the fibers so that the amount of cladding which remains behind could be regulated by controlling the time a batch of fibers was exposed to said fluid. In the present embodiment, said fluid was FLUORINERT FC-75™ obtained from the Specialty Polymers Division of the DuPont Company. Fibers were exposed to FLUORINERT FC-75™ for about thirty to about forty-five minutes. The fibers were then quickly rinsed twice with additional FLUORINERT FC-75™ and once with methanol and fibers and reservoir were placed in the entry chamber of a dry box and dried under vacuum for 30 minutes. This procedure produced fibers having a surface which was clean except for a network of hydrophobic regions of amorphous copolymers of perfluoro (22,dimethyl-1,3 dioxole) and tetrafluoroethylene) which remain. Said network of hydrophobic regions prevent large protein molecules from reaching the surface of the fiber, while permitting small molecules used in subsequent chemical sensitization of fibers to reach and react with the bare fiber surface.

Unless otherwise indicated, all reagents used in the reactions which result in sensitized fibers were obtained from Sigma Chemical Co. P.O. Box 14508, St. Louis, Mo. 63178. The fibers and reservoir were transferred into the dry box and the longitudinal surfaces of the fibers were surrounded by a 2% solution of 3-(mercaptopropyl)-trimethoxysilane in anhydrous toluene (Sigma Chemical Co.) for 2 hr at room temperature, creating a glass surface bearing thiol groups. After rinsing in toluene, the thiol groups on the fibers were reacted with the maleimido moiety of the heterobifunctional agent, γ-maleimidobutyric acid-N-hydroxysuccinamide ester, hereafter referred to as GMBS (Sigma Chemical Co.) by incubating them in a 2 mM solution of GMBS in anhydrous denatured ethanol (Sigma Chemical Co.) for 1 hr. At this point the methods for the two different types of fibers diverges. For the estrone-3-glucuronide fibers, the succinimide ester of the GMBS is reacted with a 1 mg/ml solution of hexane diamine for 4 hr at room temperature in 0.1 M carbonate buffer, pH 9.3. Following this, 15 mg of estrone-3-glucuronide (Sigma Chemical Co.) and 450 mg of 1-ethyl-3-(3-dimethylaminopropyl)-carbodiimide) were dissolved in water, pH 4.3–4.6 and the fibers were incubated with this solution overnight at room temperature.

In a variant of this preferred embodiment, the carrier is placed in the cylindrical reservoir and a top cover is placed on the reservoir so as to form a hermetic seal. In this embodiment, the reservoir is purged with a dry inert gas, such as and without limitation, dry nitrogen entering one port and leaving the other, and then fiber processing proceeds as described above with the exception that the reservoir becomes the "dry box" and is used to prevent moisture or other atmospheric contamination from affecting fiber sensitization. Thus, in this embodiment, the ports are used for injecting and removing fluid and for drying the fibers by placing the reservoir under vacuum or by purging the reservoir with inert drying gas.

Component 1a Type 2: Preparing Fibers Having an ERE Surface Feature

The nucleotide sequence of the estrogen response element from Xenopus Vitellogenen A2 Gene in known to bind the human estrogen receptor protein. Discussion of this may be found in a journal article by Wittliff, J. L., Wenz, L. L., Dong, J., et al., *Expression and Characterization of an Active Human Estrogen Receptor as a Ubiquitin Fusion Protein from Escherichia coli,* J. Biol. Chem. 265(35), 22016–22022 (1990). This text is fully and completely incorporated herein by reference, word for word and paragraph for paragraph. That nucleotide sequence will hereafter be referred to as "the ERE." It is shown below:

'5 GTCCAAAGTCAGGTCACAGTGACCTGATCAA GTT3'
'3 CAGGTTTCAGTCCAGTGTCACTGGAC-TAGTTTCAA 5'

A nucleotide of this description, which also incorporated an amine on the G residue of the 5' end of one strand was synthesized by Research Genetics, Inc., 2130 Memorial Parkway SW, Huntsville, Ala. 35801. The stands were annealed as follows:

100 μg each of the upper and lower oligo were combined in 500 μl of a buffer containing 50 mM Tris buffer pH 7.5, 50 mM KCl and 10 mM MgCl$_2$ and gently vortexed. The tube was floated in 500 ml of hot water (80° C.–90° C.) and allowed to slowly cool for two hours. To this was added 55 μl of 3.0 M NaOAc. The mixture was vortexed and split between two tubes. To each tube was added 830 μl of cold 100% EtOH. The mixture was vortexed, incubated at −20° C. for two hours and centrifuged for 15 minutes in a microcentrifuge in a cold box. The supernatant was removed and the DNA dissolved in 50 ml. Carbonate buffer for coupling to fibers.

For creating optical fibers having ERE covalently linked to the surface the fibers were prepared, cleaned and silanized with 3-(mercaptopropyl)-trimethoxysilane in dry toluene followed by GMBS as previously described. Following this 200 μg of the ERE was dissolved in carbonate buffer, pH 9.3 was injected into the fiber processor and incubated for 4 hours at room temperature. Following this fibers were washed and stored as previously described.

Fibers were rinsed with distilled water, dried with nitrogen and mounted in flow through sensor cartridges of the type shown in FIG. 1. To prevent fluorophore from leaking onto the distal or proximal fiber faces and generating spurious fluorescence, the holes were fibers emerge from the cartridge ends were sealed using 5 minute epoxy. Cells were stored at room temperature until used.

Component 2a: The Optical Apparatus for Use with an Evanescent Wave Sensor Cartridge The optical apparatus shown in FIG. 2 is designed to excite the fluorophore-tagged receptor (e.g. Cy5-tagged) bound to the surface of the fiber sensor by means of an evanescent field which is created when light is injected into a waveguide at or near the critical angle, to filter out the exciting wavelength and to collect fluorescence returning back through the optical focusing components of the apparatus and focus it into a photodetector. The design of this apparatus represents an improvement over the prior art in that it improves the signal-to-background ratio of certain fluorescence detection schemes that utilize relatively broad band excitation sources, e.g. diode lasers, with subsequent band-stop filters to reject the excitation source light in favor of the induced fluorescence prior to its detection by a photo-sensitive element.

In this apparatus, a dispersive element, e.g. a grating or prism (20), is placed in the optical path of a light beam from a light source such as and without limitation, a laser diode (21) to be subsequently directed upon a fluorescence sample, such as and without limitation, an evanescent sensor (10). The light is angularly dispersed by the element as a function of its wavelength and directed by a turning mirror (22) through blocking element(s) (23), such as and without limitation, a slit or aperture, which are utilized to select a desired wavelength bandwidth (24) and reject others (25). The selected excitation wavelengths have thus been spectrally narrowed so as to be more completely blocked by a subsequent band-stop filter (26) that prevents its impingement upon a photo-detector (27). The Littrow or near Littrow configuration of a diffraction grating is a preferred embodiment of the invention because of its high optical diffraction efficiency. An embodiment wherein a narrow turning mirror is used to select a wavelength instead of blocking elements is proposed. Light of the desired wavelength (24) is reflected by a turning mirror (28) and focused by coupling lens(s) (29) into an annularizing optical fiber (17) of a type described in patent application Ser. No. 08/616,576 entitled Surface Treatment and Light Injection Method and Apparatus. This text is fully and completely incorporated herein by reference, word for word and paragraph for paragraph. This annularizing fiber injects an annular ring of light at an angle at or near the critical angle for evanescent sensor (10) which creates an evanescent field in sensor (10), exciting fluorescence which has been bound to said sensor. Light from the fluorescence passes back though sensor (10) and through the annularizing fiber (17), is collimated by coupling lens (29 and passes through band-stop filter (26), such as and without limitation a holographic notch filter, which blocks light having wavelength of the excitation light (28) from passing. Fluorescence is focused through condensing lens (30) onto photo-detector (27) which creates an electronic signal that is processed by the apparatus of component 10a.

Component 3a: Assembly of the Sensor Cartridge

Sensitized fibers of component 1a were rinsed with distilled water, dried with nitrogen and mounted in flow through sensor cartridges of the type shown in FIG. 4. The capillary flow tube (2) of the cartridge has and O.D.=1.2 mm. It was sealed into the fluid ferrules (8) by means of an O-ring (3) The black polyimide on the ends of the fiber (5) protect the amorphous copolymers of perfluoro (2,2-dimethyl-1,3 dioxole) and tetrafluoroethylene (e.g. Teflon AF™) (7) beneath it from being scraped off when the fiber is inserted through the hole in the fluid ferrules. This is important in order that light not be scattered out of the fiber at these points as has been thoroughly explained in patent application Ser. No. 08/616,576. To prevent fluorophore from leaking onto the distal or proximal fiber faces and generating spurious fluorescence, fiber ends were be sealed to the sample cell using epoxy (6). Fluid entry ports (4) allow insertion of a needle for injection of fluids. Cartridges were stored at room temperature until used.

Component 4a: The Means of Positioning the Waveguide Sensor Cartridge

The sensor cartridge was positioned using the apparatus (19) shown in FIG. 3. In this apparatus the sensor cartridge (10) is pressed into a mounted V-block (13) such that spring-loaded needles which connect to a fluid inlet tubes or syringes (16) are pressed tightly into the fluid inlets of the sensor cartridge and sealed against an O-ring by the closing of supports (10) which are hinged onto V-block (13). A slide (12) which is mounted on the optical apparatus, allows the amorphous copolymers of perfluoro (2,2-dimethyl-1,3 dioxiole) and tetratluoroethylene (e.g. Teflon AF™)-protected end of the fiber (7) to be coupled to annularizing input fiber (17) by means of a capillary coupler (15) into which the fiber end slides and butts up against the end of input fiber (17). Input fiber (17) is of a type described in patent application Ser. No. 08/616,576 entitled Surface Treatment and Light Injection Method and Apparatus. This text is fully and completely incorporated herein by reference, word for word and paragraph for paragraph. Capillary coupler (15) is mounted in a position by support plate (18) so that the end of the fiber sensor naturally enters the lower end of coupler (15) when V-block (13) is raised by means of slide (12). The sensor cartridge is maintained in position in the coupler by tightening a screw at the lower end of the slide.

Component 5a: A Means of Acquiring Data from the Optical Apparatus

A Macintosh™ Powerbook was programmed using LabView™ software from the National Instruments Company so that the laser diode is modulated on and off every 2 seconds for the first 10 seconds and every 4 seconds for the next 74 seconds and the readings from a Stanford Research Systems Model SR810 DSP lock-in amplifier are obtained using a GPIB interface card.

Component 6a: Preparation of Cy5-Tagged-Estrogen-Receptor Solutions

Dr. James L. Wittliff, director of the Hormone Receptor Laboratory at the James Graham Brown Cancer Center of the University of Louisville provided yeast recombinant human estrogen receptor preparations. This was produced by fusion of the receptor gene with ubiquitin with subsequent over expression in yeast under the control of the Cupl promoter as previously described in the literature. (Wittliff, J. L., Dong, J., Schaupp, C., Folk, P, Butt, T. R.; "Characteristics of the Human Estrogen Receptor Protein Produced in Microbial Expression Systems," Steroid Hormone Receptors: Basic and Clinical Objects, ed. V. K. Moudgil. Hormones in Health and Disease, (Boston: Birkhauser, 1993), pp. 473–501. This text is fully and completely incorporated herein by reference, word for word and paragraph for paragraph.

Expression of Human Estrogen Receptor in Yeast

*Saccharomyces cerevisiae* strain AF103 was transformed with the YEpElO plasmid containing the ubiquitin-human estrogen receptor gene-fusion and grown in CM-Trp media with 10 mM $CuSO_4$ as described by Wittliff J. L., Dong, J., Schaupp, C., Folk, P, Butt, T. R. In V. K. Moudgil, Ed., Steroid Hormone Receptors: Basic and Clinical Objects, pp. 473–501, 1993 and in Graumann, K., Wittliff, J. L., Raffelsberger, W., Miles L., Jungbauer, A. and Butt, T. R., *Journal of Steroid Biochemistry and Molec Biol.* 57:293–300; 1996. This text is fully and completely incorporated herein by reference, word for word and paragraph for paragraph.

The yeast were grown with agitation at 30° C. in 700 ml of media using 2.8 L Fernbach flasks until the $OD_{600}$ nm reached 0.73–0.75 (i.e. late log phase). Induction was performed by adding CuSO4 to a final concentration of 100 mM and growing the cells for an additional 2 hrs. Alternatively, untransformed yeast (*Saccharomyces cerevisiae* AF103, host strain) were grown in YPD media (Ausubel et al., Current Protocols in Molecular Biology) and harvested at an $OD_{600}$ nm reading of 0.90–0.93.

Cells were harvested by centrifuging the cultures for 5 minutes at 4000 g in a HS-4 rotor (Sorvall) and washed by resuspending first in 100 mM KCI and, after subsequent centrifugation, resuspending in $P_{50}$EGMo buffer (50 mM $K_2HPO_4$, 1.5 mM EDTA, 10% glycerol, 10 mM $Na_2Mo_4$, pH 7.4). All of the following steps were performed on ice. Yeast pellets were resuspended in 2 pellet-volumes of freshly prepared lysis buffer containing 10 mM monothioglycerol and 1 mM PMSF. Aliquots (1.5 ml) of the suspension were pipetted into tubes containing 1.5 ml of glass beads (0.5 mm diameter). Using a Vortex mixer, the yeast cells were beaten 5 times for 30 sec and allowed to cool on ice (minimum of 30 sec) between each round of agitation to extract the receptor protein. A hole was punched in the bottom of each tube and the extract was drained into a 2 ml tube and centrifuged 1100 g at 4° C. in, a Beckman TJ6 centrifuge. Supernatants were collected for preparation by ultracentrifugation. Pellets of unbroken yeast cells were resuspended in lysis buffer and extracted again.

The supernatants from the low speed separation step were centrifuged in a Beckman L8-M ultracentrifuge using a 50.2 rotor for 30 minutes at 100,000 g. After centrifugation, the supernatants were removed, avoiding the lipid layer on the surface. The protein concentration was determined using the Biorad reagent (Hercules, Calif.) with the Bradford assay. Receptor binding capacity was measured by association with radio-labeled estradiol-17β in the presence and absence of unlabeled diethylstilbestrol and analyzed by the One-Site® program (Lundon Software, Inc.). Receptor content was measured by enzyme immunoassay using a sandwich-type procedure. Integrity and size of the human recombinant, estrogen receptor was evaluated by Western blot analysis using a variety of monoclonal antibodies. These preparations were used for subsequent purification steps.

Cy5-Tagging of Recombinant Human Estrogen Receptor

Buffer content and conditions of yeast extracts containing estrogen receptor were changed using open column chromatography with Sephadex 100 as the stationary phase and 0.1 M potassium carbonate buffer at pH 9.3 containing 1.5 mM EDTA, 10 mM molybdate, and 10% glycerol as mobile phase. The eluent was collected as 1.2 ml fractions and the protein content was measured using a Bradford protein assay. The first 15–20 fractions contained the high molecular weight proteins including the 65 kDa human estrogen receptor. Fractions exhibiting receptor activity were pooled and incubated with the content of 1 vial Cy5 fluorescent dye (Amersham, Arlington Heights, Ill.) for 2 hours at −4° C. To stop the reaction, an, equal volume of $P_{50}$EGM buffer, pH 6.5, containing 1 mg/ml casein was added, aliquoted into smaller volumes and frozen at −80° C. In certain experiments the ligand binding activity of the Cy5-tagged preparations were determined to evaluate the influence of the dye.

Purification of Human Recombinant Estrogen Receptor by HLPC

Estrogen receptor proteins in yeast extracts were first partially purified by size exclusion chromatography using Sephacryl S 300 (Sigma, St. Louis, Mo.) as the stationary phase and $P_{50}$EGMo buffer (50 mM $K_2HPO_4$ buffer, pH 7.4 containing 1.5 MM EDTA, 10% glycerol, 10 mM $Na_2Mo_4$) with 100 mM KCI as mobile phase. The eluent was collected as 1.2 ml fractions and the protein content of each was measured using a Bradford protein assay. Analysis of the protein concentrations of the various fractions revealed two major peaks with variable quantities of estrogen receptor activity. The fractions representing the higher molecular weight peak were pooled and an equal volume 3.8M ammonium sulfate was added just prior to injection in a Beckman HPLC unit. Synchropako Propyl-300 hydrophobic interaction chromatography column (SynChrom, Inc., Lafayette, Ind.) was used as the stationary phase and elution was performed with a gradient of ammonium sulfate ranging from 2.0–0.0M in $P_{50}$EGMo buffer at pH 7.4. Sample aliquots were evaluated using the Bradford protein assay. Western blotting and ELISA were used to determine the fractions containing human estrogen receptor. These active receptor preparations were pooled, used in certain labeling experiments or immediately frozen on dry ice and stored.

This receptor preparation is sufficiently stable to permit its use in the 15 minute room temperature protocol employed in obtaining fiber optic sensor data. The preparation was shown to exhibit hormone binding characteristics similar to those of the wild type receptor including ligand affinity ($K_d$ value= $10^{-10}$–$10^{-11}$ for estradiol-17β) and specificity (affinity constants and competitive behavior of a variety of naturally occurring estrogens and therapeutic estrogen mimics similar to wild type receptor). The yeast preparation, which contained 1 μg of hER protein per mg of total protein, was diluted with 50 mM phosphate buffer pH 7.5, containing 10% glycerol, 500 mM KCI, 2 mM dithiothreitol, 1 mM EDTA, 1 mM sodium vanadate, 0.02% sodium azide (hereafter referred to as "receptor buffer") to give a total receptor concentration of $1.1 \times 10^{-10}$M.

This solution comprised said calibration standard of component 6a. The other proteins in the yeast preparation included heat shock proteins which stabilized the hER in solution. This receptor preparation was used as the calibration solution. Immediately after preparation it was pipetted in 135 μl aliquots into microcentrifuge tubes, snap frozen and stored at −80° C. They were not thawed again until they were used with the fiber sensor. Sample solutions of component 6a were similarly prepared excepts that the dilution at the end with receptor buffer gave a total receptor concentration of $4.4 \times^{-10}$M. If the solution was to be used with an ERE fiber (component 1a type 2), then polydeoxyinosinic-deoxycytidylic acid sodium salt was added to the receptor buffer to prevent nonspecific binding to the ERE fiber. Solutions containing $4.4 \times 10^{-10}$M Cy5-tagged-estrogen-receptor solution and in addition to a predetermined amount of estrogen or estrogen mimic were created to test the impact of said estrogen or estrogen mimic.

Aliquots of 135 μl of both calibration standard or sample receptor solutions having no added ligand were pipetted into microcentrifuge tubes and frozen. Immediately upon thawing, to each 135 μl of sample solution was added 15 μl of a concentration of the test compound so as to bring the final concentration of test compound in the aliquot to either 0M, $2 \times 10^{-10}$M, $7 \times 10^{-}$M, $2 \times 10^{-9}$M, $7 \times 10^{-9}$M, $2 \times 10^{-8}$M, $7 \times 10^{-8}$M, $2 \times 10^{-7}$M, $7 \times 10^{-7}$M or $2 \times 10^{-6}$M.

Component 7a: Preparation of Solution of Cy5 Fluorophore for Measuring Scatter Background from the Calibration and Sample Solutions Cy5 which had not coupled to the receptor and which was recovered as the component passing through a Centricon 30 concentrator after a protein had been tagged with Cy5, was diluted with receptor buffer so that it gave an absorbance at 650 nm equivalent to that of component calibration standards or sample solutions. These solutions were used to evaluate scatter background from the sensor during measurements.

Method of Utilizing the First Preferred Embodiment to Identify Estrogen Mimics

All fiber sensors were subjected to identical protocol comprised of:

1) The sensor cartridge was mounted in the positioning apparatus and focused so that light from the laser diode enters the fiber at or near the critical angle.
2) A solution of 1% casein was injected into the sensor.
3) Sensor background was measured.
4) An aliquot of calibration standard and an aliquot of sample solution were removed from the freezer and thawed at 23° C. 15 μl of test sample was added to the sample solution aliquot and mixed gently with a vortex to constitute a test sample solution.
5) Exactly ten minutes after the samples were removed from the freezer, the casein solution was removed and 150 μl of calibration scatter standard was drawn into the sensor and a reading taken.
6) Calibration scatter standard was removed from the sensor and 150 μl of the sample scatter standard was drawn into the sensor and a reading taken.

7) The sample scatter standard was removed from the sensor and 150 μl of the aliquot of calibration standard was drawn into the sensor and automatic data acquisition begun.

8) 84 seconds later the aliquot of component 2a was removed and the aliquot of the test sample solution was drawn into the sensor and automatic data collection continued for another 84 seconds.

9) 84 seconds later the aliquot of the test sample solution was removed and receptor buffer was drawn into the sensor and automatic data collection continued for another 10 minutes.

10) the quantities S/C were calculated for each test sample as described in step 9m procedure 1.

11) The concentrations at which the peaks occurred for estradiol and for the other test compound (diethylstilbestrol and tamoxiphen) were compared. Estradiol is known to have a $K_d$ of roughly $1.1 \times 10^{-10}$ M for the receptor. From this knowledge it can be calculated from Equation 10 that within the level of accuracy permitted by the choice of standards $$K_d (DES) = K_d (estradiol) * (2 \times 10^{-8})/(2 \times 10^{-9}) = 1.1 \times 10^{-9} M.$$

Figure 7A:
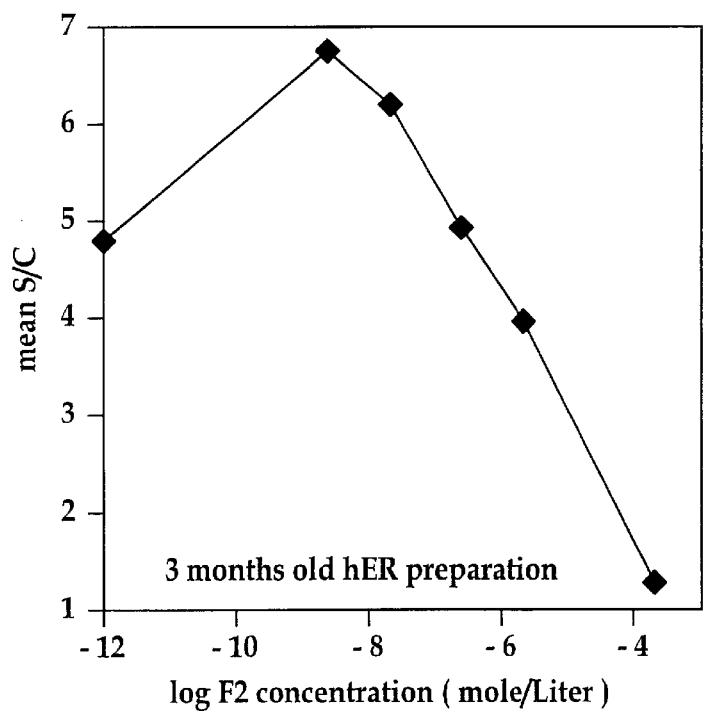
FIG. 7: Shows data obtained using the apparatus and means of this invention to assess the effects of estradiol-17β, diethylstilbestrol and tamoxifen on binding between human estrogen receptor and a sensor cartridge containing an estrone-3-glucuronide optical fiber.
Figure 7B:
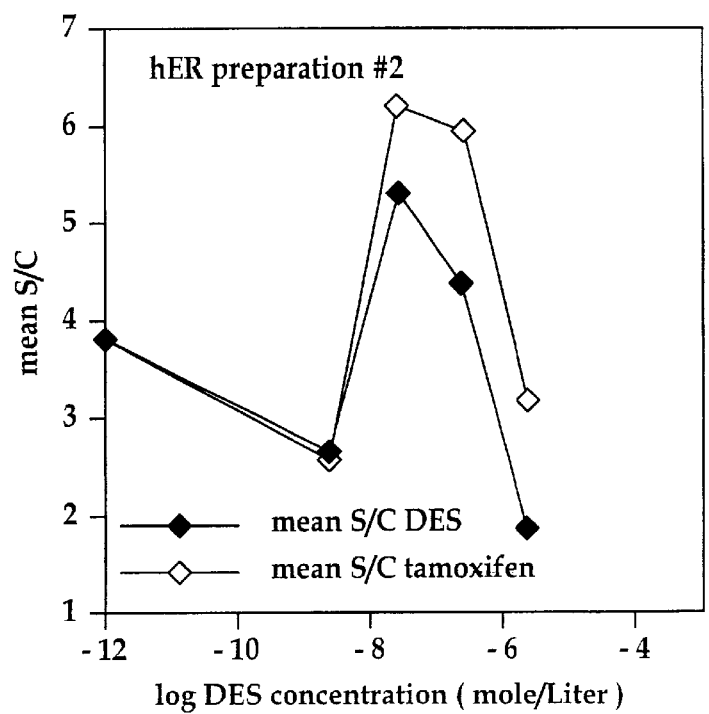

This is as close to the value of $K_d$ for DES, which is $1.8 \times 10^{-9}$ M, obtained by conventional methods, as can be expected from the choice of concentrations. The smaller the interval between choices of concentrations, the more accurately $K_d$ can be measured. Data obtained in this manner is shown in FIG. 7.

12) Using fiber sensors having a surface which resembles the nuclear response element which binds human estrogen receptor in vivo (component 1a type 2), and the foregoing procedure, the S/C value was calculated for several different estrogens tested at $10^{-6}$ M concentration. Results shown in the following table demonstrate good agreement between the known biological activity of the compound tested and the S/C value obtained for that compound using the ERE type fibers. 17β-estradiol, the strongest biological estrogen increases binding to the ERE fiber by the greatest amount. Diethylstilbestrol and zearalenone, two estrogen mimics increase binding to the ERE more than do the weak biological estrogens, estrone and estriol. Tamoxiphen, which acts as an anti-estrogen, binds to the receptor as shown in the graph above, but does not increase binding to the ERE. This is reasonable in view of its anti-estrogenic activity. Thus the combined data from the estrone-3-glucuronide fiber and the ERE fiber can be used to predict the likely biological impact of the tested compound on estrogen-mediated processes. Results are shown in the following table.

| Compound | Response of ERE fiber to hER and $10^{-6}$ M compound (control = 3.51) | Type of bioactivity |
| --- | --- | --- |
| 17β-estradiol | 7.08 | strong natural estrogen |
| estrone | 4.44 | weak natural estrogen |
| estriol | 4.25 | weak natural estrogen |
| diethylstilbestrol | 4.87 | strong synthetic estrogen |
| zearalenone | 5.01 | synthetic estrogen |
| tamoxifen | 3.35 | synthetic anti-estrogen |

The Second Example of the Preferred Embodiment

The Second Preferred Embodiment of the present invention utilizes components adapted to measurement of estrogen receptor in a tumor tissue biopsy sample to assess the probable impact of tamoxifen on the cancer represented by that sample. In this embodiment, the procedures and components of the apparatus are similar to those of the first embodiment with the addition of a type 3 fiber sensor and other changes which are described as follows.

Component 1a Type 2: Preparation of Fibers Having an ERE Surface Feature

These fibers are prepared as described under the first preferred embodiment of this invention.

Component 1a Type 3: Preparation of Fibers Having an Anti-Estrogen Receptor Surface Optical fibers were created as described under component 1a type 1 up through the addition and removal of GMBS. At this point, anti-estrogen receptor antibody such as ER1D5, obtained from Immunotech, Inc., Westbrook, Me., was diluted to a concentration of 0.05 mg per ml and the solution is injected into the fiber processor for 2 hr. at room temperature. Fibers are washed and mounted in sensor cells as previously described.

Component 6a Type 2: Preparation of Cy5-Tagged Anti-Estrogen Receptor Solutions

The recombinant estrogen receptor described in preferred embodiment #1 is used as a control sample. The sample being tested is prepared from frozen tissue biopsy by homogenization in the previously described buffer followed by centrifugation to yield a cytosol extract. These methods are known to those skilled in the art of tissue biopsy preparation. The cytosol is incubated for 10–60 minutes in the presence of Cy5-tagged anti-receptor antibody. Antibody is chosen so that it does not interfere with either ligand binding or binding to the ERE.

Dilutions of the anti-endocrine agent which is being tested as a possible treatment for the cancer represented by the sample being tested are added to samples of tissue biopsy extract. This preparation is then used in the context of sensors containing component 1a type 2 and 1a type 3 according to the procedures described for the first embodiment and data is processed by taking calculations as far as determination of S/C without the anti-endocrine compound and in the presence of various dilutions of the said compound. The data from sensors containing component 1a type 3 will confirm the estrogen-positive status necessary for anti-endocrine therapy to be a reasonable option. Significant reduction of the value of S/C from the sensor containing component 1a type 2 in the presence of the anti-endocrine compound A compound shows a good likelihood that said compound will be an effective treatment for the cancer represented by the sample. In cases where resistance to treatment has developed, the S/C value will be expected to rise back from its previously suppressed value unless the suppression results from a mutation in the estrogen response element.

The Third Example of the Preferred Embodiment

In a third embodiment of the current invention, the apparatus is configured so as to identify the presence of abnormal p53 protein in a tissue biopsy sample. The p53 protein is a regulatory molecule which, after dimerization (or perhaps dual dimerization), binds to its nuclear response element, resulting in transcription of the p21 protein. The p21 protein then inhibits Cyclin dependent kinase II thereby preventing DNA replication and stopping cell growth. Competent p53 protein is a primary natural protection against the growth and proliferation of cancer. When p53 is mutated so that its ability to initiate p21 transcription is reduced, then cancer is more likely to result when further DNA damage occurs. This is compounded by the fact that mutant p53 proteins act as dominant negative mutations (*Oncogenes*, Geoffrey M. Cooper, pp 146–147), thus, preventing healthy p53 proteins from binding to the DNA. New cancer therapies are being directed against cells containing mutant p53. This embodiment of the invention allows identification of cells producing p53 which is less than normally competent without necessitating more time-consuming PCR techniques with gel electrophoresis and DNA probes.

This embodiment utilizes a fiber of component 1a type 4 comprising a feature which binds p53 such as and without limitation, an anti-p53 antibody and a second fiber sensor utilizing a component 1a type 5 comprising a feature resembling the DNA sequence to which p53 binds in order to initiate signal transduction. This sensor assesses wild-type p53 binding to its response element in the presence of tumor extract to determine the extent of competition between wild-type and any mutant proteins in the sample, while the first sensor assesses the amount of p53 in the sample relative to the amount of displaced wild-type protein. Comparison of the ratio of these quantities for wild type p53 preparations and tissue biopsy preparations reflects the competence of the p53 produced by those cells and indicates whether the cancer is a candidate for therapies which target cells lacking normal p53 function. There are no ligand binding studies in this embodiment because p53 is a regulatory molecule which is not a receptor and therefore ligand binding measurements are irrelevant to this embodiment. Procedures and data processing for this embodiment are likewise simplified in that S/C is calculated for only the zero standard (no ligand present) with both fibers. Components are as described in the first embodiment with the following exceptions:

Component 1a Type 4: Preparation of Fibers which Bind P53

Optical fibers were created as described under component 1a type 1 up through the addition and removal of GMBS. At this point anti-p53 antibody is diluted to a concentration of 0.05 mg per ml and the solution is injected into the fiber processor for 2 hr. and room temperature. Fiber are washed and mounted in sensor cells as described under component 1a.

Component 1a Type 5: Preparation of Fibers with DNA which Binds to P53

Fibers having a surface feature resembling the nucleotide sequence which binds the p53 protein and results in transcription of p21 protein.

The nucleotide sequence of the p53 response element known to bind the p53 protein is described in an article by Yunje Cho, Svetlana Gorina, Philip D. Jeffrey and Nikola P. Pavletich appearing in the journal *Science*, volume 265, Jul. 15, 1994. This text is fully and completely incorporated herein by reference, word for word and paragraph for paragraph. This sequence is synthesized in a manner which places a reactive amine at the end of one of the nucleotide chains so that it may be coupled to the fiber surface by means identical to those described for component 1a type 2 of the first embodiment of this invention.

Components 6a: Preparation of Cy5-Tagged-P53 Solutions

Wild type p53 protein is obtained from cytosol extract of tissue biopsy homogenate by means known to those skilled in the art and is used as a control sample. The cytosol is incubated for 10–60 minutes in the presence of Cy5-tagged high affinity anti-p53 antibody. Antibody must be chosen so that it does not interfere with the dimerization process for p53 which precedes binding to its nuclear response element. It must also be directed away from the portion of the p53 molecule which is involved in the binding to the nuclear response element. Purification of the sample from the homogenate will take place by, but is not limited to, passing the homogenate containing the antibody-p53 complex through a cooled centrifugable protein A column. The complex will be desorbed using, but not limited to, traditional methods of desorbing antibodies from protein A columns as stated in *Antibodies: A Laboratory Manual,* by Ed Harlow and David Lane pp.309–311.

The calibration standard uses a stabilized sample of Cy5-tagged wild type p-53 protein which is diluted to roughly ¼ the concentration of wild type receptor in a typical tissue homogenate for the sample of a similar origin to the one being tested. The sample being tested is prepared from frozen tissue biopsy by methods similar to those used in preparation of tissue biopsy samples. It is added to a concentration of said Cy5-tagged wild type receptor expected in a typical tissue homogenate for the sample of a similar origin. A control sample consists of a concentration of said wild type receptor expected in a typical tissue homogenate for the sample of a similar origin to which is added, but not limited to, cytosol or homogenate extract of the wild type of the tissue in question. After a brief incubation time these sample will be used to assess p53 viability of the tumor. If the sample p53 is of a damage mutant type, its presence in the sample will reduce the S/C value from that obtained in the control sample.

What is claimed is:

1. An apparatus to monitor the binding affinity between a plurality of a certain molecule of a first type and a plurality of a certain molecule of a second type, said apparatus comprises:
   (a) A light source which generates and transmits a certain light signal;
   (b) Annularizing means by which a substantially uniformly distributed and cylindrical beam of light containing an initial first amount of light power and which is impingent upon said annularizing means becomes topologically transformed with minimal loss of said initial first amount of light power into an emergent second beam which is substantially uniformly distributed in power within an annular shell or region on the outside of the beam, the inside region being substantially devoid of light power;
   (c) An optical fiber waveguide which receives said transmitted light signal in which an evanescent field is generated and having said plurality of a certain molecule of a first type affixed to its lateral surface;
   (d) processing means, connected to said light source and to said waveguide for using said evanescent field to determine said binging affinity.

2. The apparatus of claim 1 wherein said molecule of a first type comprises at least a portion of a specific nucleotide, said molecules of a second type comprises at least a portion of a specific protein.

3. An apparatus of claim 2 wherein said specific protein is a biological receptor and said specific nucleotide is a response means for said receptor.

4. An apparatus of claim 1 wherein said molecules of a first type resemble a ligand and said molecules of a second type comprise at least a portion of a specific protein having affinity for said ligand.

5. An apparatus of claim 4 wherein said specific protein is a biological receptor.

6. The apparatus of claim 1 wherein said molecules of a second type further comprises a molecular tag which when bound to said optical waveguide, produces an alteration in a certain characteristic of light collected from said waveguide in response to said generated evanescent field.

7. The apparatus of claim 6 wherein said molecular tag is a fluorescent molecule.

8. The apparatus of claim 6 wherein said molecular tag is a luminescent molecule.

9. The apparatus of claim 6 wherein said molecular tag absorbs light from said light source.

10. The apparatus of claim 6 wherein said molecular tag alters the polarization of light from said light source.

11. The apparatus of claim 6 wherein said molecules of a second type further comprises a molecular tag which is an enzyme capable of acting upon a substrate so as to produce a chemical substance which when bound to said optical waveguide, produces an alteration in a certain characteristic of light collected from said waveguide.

12. An apparatus of claim 1 wherein said annularizing means comprises:
(a) a large numerical aperture optical fiber cable; said optical fiber cable having sufficient length to allow an off axis beam injected by a focusing means to propagate as real modes in a substantially confined manner within said optical fiber cable becoming uniformly azimuthally distributed in higher order modes such that the beam will exit the cable as an annular cone of light, the distal end of said cable being the distal end of said annularizing device;
(b) a large numerical aperture optical focusing means located proximally to said optical fiber cable, such as, but not limited to, a lens or lens assembly, said numerical aperture being at least as large as said optical fiber waveguide, said focusing means having an acceptance aperture significantly larger than the diameter of the beam at a first narrow band of wavelengths impingent upon said annularizing device, said focusing means focusing a beam at the first narrow band of wavelengths impingent both normal to the aperture of said focusing means and substantially offset from the optical axis of said focusing means, onto the surface of said optical fiber cable.

13. An apparatus of claim 12 wherein said annularizing means includes a means for adjusting the cone angle of light emergent from said annularizing device so that the cone angle of light entering said optical fiber waveguide such that substantially all rays of light subsequently propagating through said waveguide impinges upon the side surfaces of said waveguide at the proper angle for maximum evanescent coupling of the light at the first narrow band of wavelengths to molecules bound to or near the surface of said optical fiber waveguide.

14. An apparatus of claim 13 wherein said adjusting means is mounted on a translatable mount positioned so that the axis along which translation translation occurs is perpendicular to the longitudinal axis of said focusing means.

15. An apparatus of claim 12 wherein said annularizing optical fiber is butt coupled to the proximal end of said optical fiber waveguide so as to transfer light between the two fibers.

16. An apparatus of claim 15 wherein said annularizing fiber and the side surface of the proximal end of said optical fiber waveguide are both clad with a material having a refractive index which is less than that of the material comprising said optical waveguide and approximately equal to or less than that of the said solution in contact with said waveguide.

17. An apparatus of claim 15 wherein said means of butt coupling said fibers is a coupling capillary comprising a cylindrical tube of capillary dimensions having internal radius so as to permit entry of said clad fibers into the interior of said capillary while constraining the position of said fibers in all directions outward from the radial center of said fibers.

18. An apparatus of claim 16 wherein said processing means comprises:
(a) collecting means for collecting fluorescence from said optical fiber waveguide wherein fluorescence exits the proximal end of said optical fiber waveguide, enters the distal end of said annularizing means, propagates through the cable, is collected in its entirety by a annularizer focusing lens, the numerical aperture of the lens being as large or larger than the numerical aperture of the cable, and is converted into a nearly parallel beam of light containing the desired broad band fluorescence to be measured as well as light at the first narrow band of wavelengths which was reflected from or scattered by a surface within the optical apparatus or fiber sensor;
(b) removing means for removing substantially all light at the first narrow band of wavelengths from the parallel beam of light, such as, but not limited to, a holographic notch filter;
(c) detecting means for detecting the remaining fluorescence the beam of light such as but not limited to a photodiode or photomultiplier which are connected to a plurality of detection electronics appropriate for maximizing signal detection when using modulated or pulsed light sources.

19. An apparatus of claim 12 including means for positioning said fiber optic waveguide with respect to a coupling capillary, said means being adapted to slide said fiber optic sensor cartridge into said coupling capillary.

20. An optical sensing apparatus of claim 19 in which an additional means of narrowing the bandwidth of the first wavelength employs a narrow band filter selected from that category of filters which includes multi-layer interference filters and holographic filters, said addition means being situated such that light propagating from said light source impinges on and passes through said additional means of narrowing.

21. An optical sensing apparatus of claim 19 further including additional means for narrowing the bandwidth of the first wavelength using a narrow band filter selected from the group consisting essentially of multi-layer interference filters and holographic filters, said addition means being situated such that light propagating from said light source impinges on and passes through said additional means of narrowing.

22. An apparatus as in claim 19 in which said directing means is a mirror whose cross sectional area is very much smaller than the area of the proximal face of the annularizing device.

23. An apparatus of claim 12 wherein said light source includes means for generating a first narrow band of wavelengths for stimulating fluorescence in molecules at a second band of wavelengths, said narrow band providing improved discrimination between the first narrow band of wavelengths and the fluorescent signal emitted by the fluorescently tagged molecules, said means comprising:
(a) dispersing means for dispersing said light, said dispersing means situated such that light propagating from said light source impinges upon said dispersing means, said impingent light propagating such that each constituent wavelength component of light is angularly dispersed as a function of wavelength so as to angularly separate unwanted wavelength band(s) from wanted wavelength band(s);
(b) directing means for directing said angularly dispersed light along a path of substantial distance, said distance being substantial when the path length is sufficient to spatially separate unwanted wavelength band(s) from wanted wavelength band(s);
(c) Blocking means for intercepting unwanted wavelength bands, said blocking means situated at said substantial distance to said dispersing means.

24. An optical sensing apparatus of claim 23 in which an additional means of narrowing the bandwidth of the first narrow band of wavelengths employs a narrow band filter such as but not limited to a multi-layer interference filter or a holographic filter, situated such that light propagating from said light source impinges on and passes through said filter.

25. An apparatus as in claim 23 wherein said directing means is a mirror whose cross sectional area is very much smaller than the area of the proximal face of the annularizing device.

26. An apparatus of claim 1 wherein said contact between said waveguide surface and said molecules of a second type is achieved by bringing said molecules of a second type into a sensor cartridge, said sensor cartridge comprising in combination:
(a) An optical fiber waveguide, said waveguide having been at least partially stripped of its cladding in a central portion while possessing cladding along the longitudinal surface of its proximal end, and said central portion having been treated so as to hold in proximity to the longitudinal surface of said optical fiber said plurality of a certain molecule of a first type; and
(b) Fluid ferrules which position said fiber assembly within said cylindrical tube, said cylindrical tube being of capillary dimensions, said end caps possessing holes providing means through which solution may enter and exit said capillary tube, and said end caps also provided with sealing means so as to prevent leaking of said solution at points where said optical fiber and said cylindrical tube contact said fluid ferrules.

27. An apparatus of claim 26 wherein said optical fiber waveguide has a protective sheath surrounding said cladding along the longitudinal surface of its proximal end.

28. An apparatus of claim 26 wherein said optical fiber waveguide has a network of hydrophobic regions on said central portion, said regions being spaced so as to prevent large molecules from contacting the surface of said optical fiber while permitting small molecules to contact and said central surface so as to allow chemical sensitization of said central portion of said optical fiber waveguide.

29. An apparatus of claim 28 wherein said hydrophobic regions are achieved by incomplete dissolution of a hydrophobic cladding material on said optical fiber waveguide.

30. An apparatus of claim 29 wherein said cladding material is a member of a class of chemicals known as amorphous copolymers of perfluoro (22, dimethyl-1,3 dioxole) and tetrafluoroethylene and said dissolution is achieved by means of a solvent belonging to that class of chemicals known as perfluoroalkanes.

31. An optical apparatus of claim 1 comprising in combination:
(a) A light source which generates and transmits a certain light signal;
(b) A dispersive element situated such that light propagating from said light source impinges upon said dispersive element; Said impingement light, upon exiting from said dispersive element, thereafter propagates such that each constituent wavelength component of light is angularly dispersed as a function of wavelength; Said dispersive element functions to angularly separate unwanted wavelength band(s) from wanted wavelength band(s);
(c) A means of directing said angularly dispersed light along a path of substantial distance; Said distance is substantial when the path length is sufficient to spatially separate unwanted wavelength band(s) from wanted wavelength band(s);
(d) Blocking element(s) situated at said substantial distance to said dispersive element; said blocking element(s) intercepting only unwanted wavelength band(s); selected wavelength band(s) are not being intercepted by said blocking element(s), and thus, continuing to propagate;
(e) Means of directing said selected wavelength band(s) into an optical fiber at an angle so as to cause said wavelength bands to propagate as real modes in a substantially confined manner within said optical fiber such that said selected wavelength band(s) emerge from the distal end of said optical fiber in an annular ring having a certain cone angle;
(f) Means of coupling said optical fiber to a second optical fiber, said second fiber being treated so as to attach a plurality of a certain molecule of a first type, in close proximity to at least a portion of the surface of said waveguide, said surface extending in a direction parallel to the direction of transmission of said light through said waveguide, and said second fiber comprising a part of a fiber optic sensor;
(g) Means of introducing test and reagent solution(s) into contact with the surface of said second optical fiber;
(h) Means of collecting light returning from said second optical fiber and directing said light so as to allow light having a specific characteristic to be focused upon a photodetector, while reflected light from the original light source which lacks said specific characteristic is rejected; and
(i) Means for processing a signal generated by said photodetector.

32. An apparatus of claim 31 wherein said light source comprises a laser diode.

33. An apparatus of claim 31 wherein said specific characteristic of light comprises a certain wavelength bundle produced by fluorescent molecules, said fluorescent molecules having become bound to said plurality of molecules held in close proximity to the surface of said second fiber.

34. An apparatus of claim 31 wherein said certain cone angle is such that light entering said second optical fiber generates an evanescent field at the surface of said second optical fiber.

35. An apparatus of claim 31 wherein the surface of said second optical fiber possesses a network of hydrophobic regions, said regions functioning to reduce nonspecific binding of proteins to said surface.

36. The apparatus of claim 1 wherein said certain first type of molecule is a specific nucleotide and said certain second type of molecule is a specific protein.

37. The apparatus of claim 36 wherein said specific protein is at least a portion of a biological receptor and said specific nucleotide is at least a portion of a biological response element for said biological receptor.

38. The apparatus of claim 1 wherein said certain first type of molecule is a specific ligand and said certain second type of molecule is a specific protein.

39. The apparatus of claim 1 wherein said specific protein is at least a portion of a hormone receptor and said specific ligand is a hormone known to have a binding affinity for said hormone receptor.

40. The apparatus of claim 1 wherein said biological receptor is an estrogen receptor and said specific nucleotide is an estrogen response element.

41. The apparatus of claim 1 wherein said biological receptor is an estrogen receptor and said hormone is an estrogen.

42. An apparatus of claim 1 in which said coupling means focuses light from said annularizing means into said optical fiber waveguide by means of a high numerical aperture optical relay device such as, but not limited to, optical relay devices having numerical aperture at least as large as the numerical aperture of the annularizing device.

43. An apparatus of claim 1 wherein said contact between said waveguide surface and said molecules of a second type includes bringing said molecules of a second type into a sensor cartridge, said sensor cartridge comprising in combination:
  (a) An optical fiber waveguide, said waveguide having been at least partially stripped of its cladding in a central portion while retaining for purpose of effective butt coupling, the cladding of claim 23 along the longitudinal surface of its proximal end, and said central portion having been treated so as to hold in proximity to the longitudinal surface of said optical fiber said plurality of a certain molecule of a first type; and
  (b) Fluid ferrules which position said fiber assembly within said cylindrical tube, said cylindrical tube being of capillary dimensions, said end caps possessing holes providing means through which solution enters and exits said capillary tube, and said end caps further including sealing means for preventing leaking of said solution at points where said optical fiber and said cylindrical tube contact said fluid ferrules.

44. An optical sensing apparatus for stimulating and measuring fluorescence from fluorescently tagged molecules bound to or near to the surface of an optical fiber sensor, said optical apparatus comprising:
  (a) A light source selected from the group consisting essentially of a pulsed laser, a laser diode and an LED, said light source generating a beam of light at a first narrow band of wavelengths, to be used for stimulating fluorescence at a second band of wavelengths;
  (b) narrowing means for narrowing initial bandwidth of said beam of light at the first narrow band of wavelengths to allow subsequent fluorescence detection means to better discriminate between said first narrow band of wavelengths and said second band of wavelengths, said means comprising:
    (i) A dispersive element situated such that light propagating from said light source impinges upon said dispersive element, said impingent light, upon exiting from said dispersive element, thereafter propagating such that each constituent wavelength component of light is angularly dispersed as a function of wavelength, said dispersive element also functioning to angularly separate unwanted wavelength band(s) from wanted wavelength band(s); and
    (ii) directing means for directing said angularly dispersed light along a path of substantial distance, said distance being sufficient to spatially separate unwanted wavelength band(s) from wanted wavelength band(s); and
    (iii) Blocking element(s) situated at said substantial distance to said dispersive element, said blocking element(s) intercepting only unwanted wavelength band(s) while allowing selected wavelength band(s) to continue to propagate as light possessing a narrowed bandwidth
  (c) means for directing said beam of narrowed bandwidth into an annularizing optical device which transforms the approximately cylindric beam of light impingent on the proximal end of said annularizing optical device into an annular cone of light exiting the distal end of the annularizing optical device;
  (d) annularizing means by which a substantially uniformly distributed and cylindrical beam of light containing an initial first amount of light power and is impinged upon, said annularizing means becoming topologically transformed with minimal loss of said initial first amount of light power into an emergent second beam which may be collimated, converging or diverging and is substantially uniformly distributed in power within an annular shell or region on the outside of the beam, the inside region being substantially devoid of light power; said annularizing device consisting of;
    (i) A large numerical aperture optical focusing means, said numerical aperture being at least as large as said optical fiber sensor, said focusing means having an acceptance aperture significantly larger than the diameter of the beam containing said first narrow band of wavelengths impingent upon said annularizing device, said focusing means located proximally to and focusing said beam onto the surface of a large numerical aperture optical fiber cable, the numerical aperture of said lens being as large or larger than the numerical aperture of said optical fiber cable, said focusing means including in the focusing, elements of said beam impingent normal to the aperture of said focusing means as well as elements substantially offset from the optical axis of said focusing means;
    (ii) Said optical fiber cable having sufficient length to allow the off axis beam injected by the focusing means to propagate as real modes in a substantially confined manner within said optical fiber cable and become uniformly distributed in higher order modes such that the beam exits the cable as an annular cone of light, said annular cone when projected from the distal face of the fiber upon a flat surface shows essentially all emergent light being contained in a thin ring, the thickness of such ring being far smaller than the outer ring diameter; said cable having the identical numerical aperture and diameter as said optical fiber sensor, the distal end of said cable being the distal end of said annularizing device;
  (e) coupling means for coupling the annular cone of light emergent from said optical annularizing device into said optical fiber sensor in which the proximal face of said optical fiber sensor is butt coupled (placed directly in contact with) to the distal end of said annularizing means, (f) adjusting means for adjusting cone angle of light emergent from said annularizing device such that the cone angle of light entering said optical fiber sensor is adjusted so that substantially all rays of light subsequently propagating through said optical fiber impinge upon the side surfaces of said optical fiber sensor at the proper angle for maximum evanescent coupling of the light at the first narrow band of wavelengths to fluorescent molecules bound to or near the surface of said fiber sensor;

(g) collecting means for collecting fluorescence from said optical fiber sensor wherein fluorescence exits from a proximal end of said optical fiber sensor and enters a distal end of said annularizing means, propagates through a cable, is collected in its entirety by said focusing means, and converted into a nearly parallel beam of light containing the desired broad band fluorescence to be measured as well as light at the first narrow band of wavelengths which was reflected from or scattered by a surface within the optical apparatus or fiber sensor;

(h) blocking means for blocking substantially all light at said first narrow band of wavelengths from said parallel beam of light, said blocking means selected from the group consisting essentially of a holographic notch filter and like filters; and (i) detecting means for detecting fluorescence, said detecting means selected from the group consisting of a photodiode and a photomultiplier connected to a plurality of detection electronics appropriate for maximizing signal detection when using modulated or pulsed light sources selected from the group consisting essentially of analog to digital converters, synchronous detectors, lock-in amplifiers, and photon counters.

which may be electronically modulated to increase detection sensitivity.

45. An apparatus of claim 44 wherein said butt coupling is replaced by or coupled by means of an high numerical aperture optical relay devices, said numerical aperture of said optical relay devices being at least as large as the numerical aperture of the annularizing device.

* * * * *